US012797031B2

(12) United States Patent
Barnacka et al.

(10) Patent No.: US 12,797,031 B2
(45) Date of Patent: Nov. 17, 2026

(54) EARBUD BASED AUSCULTATION SYSTEM AND METHOD THEREFOR

(71) Applicants: Anna Barnacka, Cambridge, MA (US); Jal Panchal, Everett, MA (US); Robert Ciesielski, New York, NY (US)

(72) Inventors: Anna Barnacka, Cambridge, MA (US); Jal Panchal, Everett, MA (US); Robert Ciesielski, New York, NY (US)

( * ) Notice: Subject to any disclaimer, the term of this patent is extended or adjusted under 35 U.S.C. 154(b) by 641 days.

(21) Appl. No.: 18/336,585

(22) Filed: Jun. 16, 2023

(65) Prior Publication Data

US 2023/0404518 A1 Dec. 21, 2023

Related U.S. Application Data

(60) Provisional application No. 63/352,954, filed on Jun. 16, 2022.

(51) Int. Cl.
*A61B 7/04* (2006.01)

(52) U.S. Cl.
CPC ........ *A61B 7/04* (2013.01); *A61B 2560/0271* (2013.01)

(58) Field of Classification Search
None
See application file for complete search history.

(56) References Cited

U.S. PATENT DOCUMENTS 3,108,652 A 10/1963 Littmann
3,276,536 A 10/1966 Littmann
8,401,217 B2 * 3/2013 Shams .................. H04R 29/00 381/345
9,579,060 B1 * 2/2017 Lisy ...................... A61B 5/165
9,867,591 B2 * 1/2018 Shams .................. A61B 5/117
10,092,269 B2 10/2018 Shams et al.
11,234,069 B2 * 1/2022 Barnacka ................ A61B 8/12
11,488,590 B2 * 11/2022 Cella .................... H04R 1/1016
11,844,618 B2 * 12/2023 Barnacka ............ A61B 5/7465
11,992,360 B2 * 5/2024 Barnacka .......... A61B 5/02116
12,003,914 B2 * 6/2024 Barnacka ............ H04R 1/1041
(Continued)

OTHER PUBLICATIONS

Digital stethoscope: technology update; Swarup, Supreeya and Makaryus, Amgad; Medical Devices: Evidence and Research 2018:11 29-36.

*Primary Examiner* — Shirley X Jian
(74) *Attorney, Agent, or Firm* — Gillis Patent Law, LLC; John Gillis

(57) ABSTRACT

An earbud based auscultation system and method therefor are disclosed. The system includes a signal detector and a network interface. The signal detector includes a body that accepts an earbud, and a base of the body is positioned against a body of a patient and receives biosignals from the patient. The earbud includes sensors that detect the biosignals including infrasonic and audible signals via the base and sends the biosignals to the network interface, which forwards the biosignals to a remote device such as a server. An analysis system can access the biosignals at the remote device to identify and characterize physiological processes of the patient based on the biosignals. In embodiments, a second earbud is placed in the ear canal of the patient or coupled to a second signal detector placed against the patient's body. In one example, the network interface is a wireless interface of an earbud.

22 Claims, 20 Drawing Sheets

(56) References Cited

U.S. PATENT DOCUMENTS

| | | | | |
|---|---|---|---|---|
| 12,047,726 | B2 * | 7/2024 | Barnacka | H04R 1/1075 |
| 12,440,112 | B2 * | 10/2025 | Barnacka | H04R 1/1016 |
| 2011/0125063 | A1 * | 5/2011 | Shalon | A61B 5/4205 600/590 |
| 2017/0318397 | A1 * | 11/2017 | Lim | H04R 25/48 |
| 2019/0028789 | A1 * | 1/2019 | Stockton, X | H04R 1/1058 |
| 2019/0247010 | A1 * | 8/2019 | Baracka | A61B 8/02 |
| 2021/0015442 | A1 * | 1/2021 | Barnacka | G16H 40/67 |
| 2021/0045647 | A1 * | 2/2021 | Barnacka | A61B 5/7246 |
| 2021/0051389 | A1 * | 2/2021 | Barnacka | A61B 8/12 |
| 2021/0145306 | A1 * | 5/2021 | Karankevich | A61B 5/7475 |
| 2021/0153837 | A1 * | 5/2021 | Jones | A61B 5/0205 |
| 2021/0401311 | A1 * | 12/2021 | Barnacka | A61B 5/6803 |
| 2022/0218273 | A1 * | 7/2022 | Barnacka | A61B 7/003 |
| 2023/0107691 | A1 * | 4/2023 | Barnacka | A61B 8/5223 600/484 |
| 2023/0404518 | A1 * | 12/2023 | Barnacka | A61B 7/04 |
| 2025/0195024 | A1 * | 6/2025 | Barnacka | A61B 5/029 |

* cited by examiner

Fig. 9
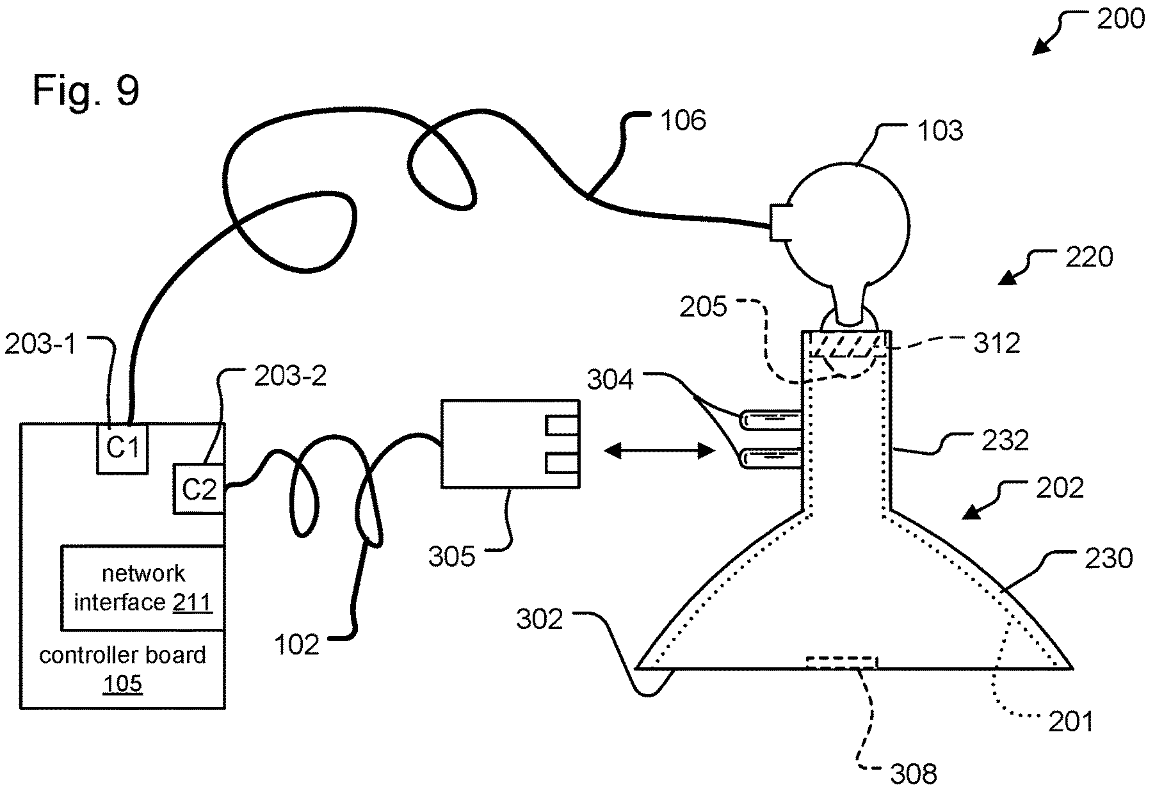
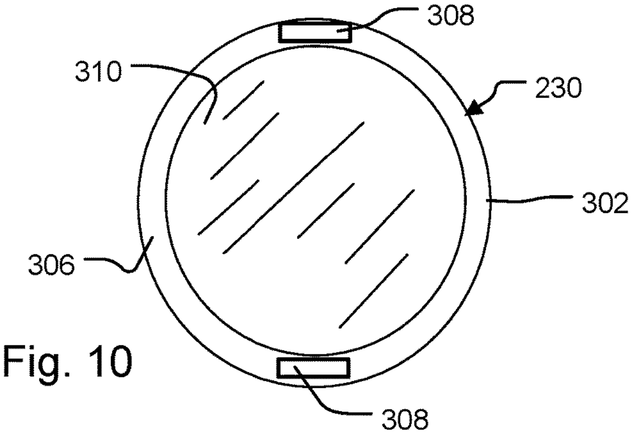
Fig. 10
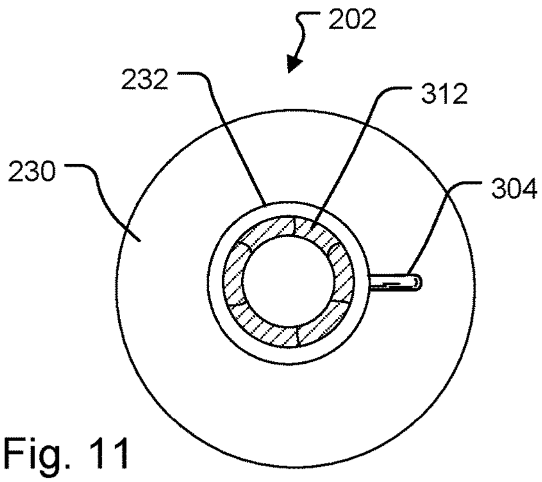
Fig. 11

EARBUD BASED AUSCULTATION SYSTEM AND METHOD THEREFOR

RELATED APPLICATIONS

This application claims the benefit under 35 USC 119(e) of previously filed U.S. Provisional Application No. 63/352,954 filed on Jun. 16, 2022, which is incorporated herein by reference in its entirety.

FIELD OF THE INVENTION

The present invention generally relates to the field of noninvasive medical monitoring devices. In particular, the present invention is directed to an earbud based auscultation system that can monitor and detect biosignals from patients and analyze the biosignals to identify and characterize physiological processes of the patients.

BACKGROUND OF THE INVENTION

Biosignals are signals in living beings such as human patients that can be detected, observed and/or measured. Examples of biosignals from patients include acoustic signals, pressure signals, thermal signals and electrical signals. The acoustic signals are created as a result of breathing and physical/mechanical operations within the patient's body. These operations include blood flow throughout the cardiovascular system, and opening and closing of valves within the heart and the blood vessels, in examples. These acoustic signals can be in either the infrasonic range (infrasonic signals) or in the audible range (audible signals) or both. The pressure signals are created by pressure or tension within the body. The thermal signals are created in response to physical and biochemical processes within the body. The electrical signals are associated with changes in electrical current over time, across a specialized tissue, organ, or cell system such as the nervous system.

Acoustic sounds include infrasounds and audible sounds. Infrasounds/infrasonic signals are sounds or acoustic vibrations with frequencies below the range of human hearing. The frequency range of infrasounds is between 0 and 20 Hz. Audible sounds/audible signals, in contrast, are sounds in a range that includes sounds greater than 20 Hz but less than about 20 KHz.

The human body is a robust acoustic sound generator. The human body generates infrasounds through various operations of the cardiovascular system and via musculoskeletal motion, in examples. The operations of the cardiovascular system that generate infrasound include myocardial contractions of the heart, arterial wall vibrations in response to blood flowing through the arteries, turbulence associated with the blood flow itself in arteries and veins, and heart valve operation, in examples. In contrast, the body generates audible sounds via the pulmonary system, digestive system, organs of speech and the heart (specifically, heart sounds S1, S2, S3 and S4).

Auscultation is the process of listening to sounds from the body of a patient. The sounds originate from the heart, lungs, other organs or blood vessels of the patient, in examples. Traditionally, auscultation is performed with a stethoscope as a part of a medical checkup or diagnosis.

Traditional binaural acoustic stethoscopes have existed since the 1850s. These traditional stethoscopes are passive devices which detect audible sounds only. Components of the traditional stethoscopes include earpieces arranged in a headset, a chest piece with a flat base, and flexible tubing that connects the chest piece to each of the earpieces.

Traditional stethoscopes operate as follows. A medical professional places the earpieces in their ears and places the chest piece upon the body of the patient, typically near the lungs and heart of the patient. The chest piece detects audible sounds of the body of the patient, and the medical professional listens to the detected sounds in real-time via the earpieces.

Over the last century, improvements to traditional stethoscopes have included making the chest pieces lighter in weight, the addition of a "bell" to the chest piece for detecting lower frequency audible sounds, and changes to the chest piece to increase the quality and amplification of the sounds obtained. These changes include the addition of a tunable diaphragm to the base, and improvements to the design of a resonant cavity within the chest piece that receives and amplifies the body sounds, in examples.

SUMMARY OF THE INVENTION

More recently, electronic stethoscopes have been proposed. These stethoscopes include microphones that convert the detected sound waves into electrical data. The electrical data can be analyzed and displayed at a computer system. In particular, one exemplary electronic stethoscope, also known as an infrascope, includes a microphone that claims the ability to detect both audible and infrasonic sounds. See U.S. Pat. No. 8,401,217B2 for the microphone and U.S. patent Ser. No. 10/092,269 for the exemplary electronic stethoscope that includes the microphone, in examples.

In the existing infrascope, the microphone has a cylindrical metal body and attaches to a chest piece-style body coupler. The coupler is placed upon the body of the patient. The microphone/body coupler combination also attaches to earpieces via flexible tubing, as in traditional stethoscopes. The infrascope allows medical professionals to hear audible sounds from the body of the patient in real-time via its earpieces, as with traditional stethoscopes, while its microphone/body coupler also sends electrical data associated with detected audible sounds and infrasounds to a computer system for analysis.

However, the existing infrascope has limitations. In one example, it is very expensive; the microphone component alone has a typical retail cost of $1450 USD. Additionally, some embodiments of the infrascope that include two microphones require a separate physical mounting structure to hold the microphones above the body of the patient. This limits the physical settings in which the infrascope can be used and increases cost. Moreover, while the tubing and earpieces allow medical professionals to hear audible sounds in-real-time, as with traditional stethoscopes, the tubing and earpieces present problems for detecting infrasounds.

The tubing and earpieces of the existing infrascope present problems for detecting infrasound because of pressure changes they cause or otherwise introduce to the air pressure inside the microphone. For example, as the tubing length increases, it takes longer for the infrascope as a whole to achieve an equilibrium pressure before optimum detection of infrasounds can occur. Moreover, the earpieces of the infrascope must have a sufficient seal at the ear canals of the medical professional in order for the microphone to best detect infrasounds. This is because improper earpiece seals introduce leaks into the preferably sealed infrascope system, causing air outside the microphone to exchange with air inside the microphone cavity. The pressure inside the microphone cavity decreases in response. The decrease in pressure correspondingly decreases the amplitude of infrasounds that enter the cavity and which the microphone can detect, and also raises the low frequency threshold of infrasound frequencies that the microphone can detect.

A novel, earbud based auscultation system is proposed. The auscultation system includes a detector system worn by a patient that includes a signal detector placed against the body of a patient. The signal detector receives biosignals including audible and infrasonic signals from the body of the patient.

The signal detector has a body that is similar in appearance to the chest piece of traditional stethoscopes. The body includes a base that is disposed against the body of the patient, and accepts an earbud including at least one sensor that detects the biosignals received at the body of the signal detector. The earbud is substantially the same as the earbud described in US Pat. Pub. No. US20190247010A1 and in U.S. Pat. No. 11,234,069, with any modifications described herein. The contents of U.S. Pat. Pub. No. US20190247010A1 and U.S. Pat. No. 11,234,069 are incorporated by reference in their entirety.

Also in the proposed auscultation system, in a preferred embodiment, each earbud is wireless and includes a wireless network interface. Via its network interface, each earbud forwards the detected biosignals to a remote device over a network. The device can be a computer system such as server, in one example. In another embodiment of the system, each earbud wirelessly connects to a network interface of a local controller board that receives, collects and buffers the acoustic biosignals from each of the earbuds. The controller board, in turn, forwards the biosignals via its network interface to the remote device over the network.

In another embodiment, each earbud connects in a wired fashion to a local controller board that receives, collects and buffers the acoustic biosignals from each of the earbuds. The controller board, in turn, has a network interface that receives and collects acoustic biosignals of the patient detected by and sent from the earbud(s) and forwards the biosignals to the remote device over the network.

The remote device includes and/or otherwise presents an application programming interface (API). The remote device is typically a computing device such an application server. The remote device can be located in or distributed across a remote network cloud, such as a public network (i.e. the Internet) or private network, or be a node on a local area network (LAN), in examples.

A data analysis system in communication with the API can then access the biosignals at the API and process the acoustic biosignals to identify and characterize physiological processes of the patient. As with the application server, the data analysis system can be located in or distributed across the network cloud, or be a node on a local area network (LAN), in examples.

The patient or another individual operates the auscultation system via an application executing on a user device such as a mobile phone or a laptop. The user device is in communication with the detection system and the API, and possibly also with the data analysis system. The app presents an interactive graphical user interface (GUI) to the patient. Via the app, the patient can configure the auscultation system to operate in different modes. In one implementation, the app (or other applications executing on the user device) can operate as the data analysis system.

To configure the auscultation system, the patient or another individual selects modules (or module types) presented by the app. The modules are associated with different operational modes of the auscultation system. After the patient selects a module, the patient places one or more signal detectors of the system upon the skin/at the body of the patient, and possibly places an earbud in an ear canal, where the number and placement of the signal detectors is specific to one or more modules/modes of the system. The patient selects an "OK" button of the app or similar facility to execute the configuration request.

After the auscultation system configures its components in accordance with the module type/mode selected by the patient, the signal detectors and/or the earbuds of the detection system detect biosignals from the body of the patient. These biosignals include infrasonic and audible biosignals, and possibly electrical and ultrasonic biosignals. The signal detectors then send an electrical representation of the detected biosignals to the local controller board, which in turn forwards the electrical representation of the biosignals and possibly other information based on the biosignals to the data analysis system. For the sake of brevity, the electrical representations of the biosignals are simply referred to as biosignals hereinafter.

During and/or based upon the analysis of the biosignals, the data analysis system can verify whether the signal detectors are adequately placed against the patient's skin, can ensure that minimal sound is lost to leaks, and determine whether the patient is moving, in examples. The placement can be assessed by sound recorded by the signal detectors, or by augmented reality via a smartphone app, in examples.

The detection system of the proposed auscultation system overcomes the limitations of the existing infrascope. In one example, the earbuds have a substantially lower cost than the microphones of the existing infrascope. Reasons for the lower cost of the earbuds include a smaller form factor, less expensive materials and the ability for manufacturers to mass-produce the earbuds, in examples. Moreover, the earbuds can be used as traditional earbuds for audio playback of music and other audible signals.

Additionally and/or alternatively, traditional active noise cancelling earbuds worn by individuals can be adapted to provide the capabilities of the earbuds in the auscultation system. For this purpose, an "eartip" adapter can be retrofitted to the traditional earbuds, in conjunction with software added to user devices carried by the individuals. The adapter includes the infrasound/vibration sensors and possibly one or more motion sensors.

The detection system also eliminates the headset, earpieces and tubing of the existing infrascope. This has multiple benefits. First, the detection system has fewer components and is simpler to manufacture, which also lowers cost. Second, because there is no tubing as in the existing infrascope, the detection system is much easier to use. The signal detectors of the detection system can not only be placed at any location of the patient's body, but also the patients themselves can perform the placement. Third, the lack of tubing and earpieces in the auscultation system eliminates the pressure tuning and pressure equalization wait time of the existing infrascope, and also eliminates a potential source of air leaks which impact infrasound detection.

The detection system of the proposed auscultation system has yet other advantages over the exemplary infrascope. In one embodiment of the detection system, a signal detector with a coupled first earbud is placed upon the body of the patient, and a second earbud (not coupled to a second signal detector) is sealably placed at an inner ear canal of the patient. In a preferred embodiment of the auscultation system, wireless earbuds are used. Wireless earbuds make the detection system even easier to use, as the lack of wires between components allows even more flexibility of placement options of the signal detectors upon the body of the patient.

Still another advantage of the auscultation system is the ability for individuals of different skill levels/sophistication to configure and operate the system. The patient themselves or another individual with the patient can configure and operate the system via an application ("app") executing on a user device such as a mobile phone or laptop. The motion sensor can help individuals of different skill levels with proper placement of the signal detectors relative to the body of the patient. The individual with the patient can be a medical professional or even a layperson with sufficient training. This has advantages in rural settings and in other locations where access to medical facilities or clinics and physical infrastructure (e.g., roads, transportation) is limited or lacking.

With the assistance of the app, the patient can establish a communications session between the app, controller board and the data analysis system and configure the auscultation system to operate in one or more different operational modes. The modes are typically associated with different physiological processes that the system is designed to detect and analyze. The modes include cardiac, lung/pulmonary, arterial and/or valvular stenosis, pulse wave velocity, and fetal heartbeat, in examples. Patient-defined modes are also supported.

The communications sessions can also be interactive. For this purpose, the data analysis system can prompt the patient via the app to perform certain mode-specific tasks or otherwise notify the patient. This might include instructing the patient to change the location of one or more signal detector upon their bodies, to check an earbud seal, to cease physical movement, or to seek medical attention upon completion of a session, in examples.

In general, according to one aspect, the invention features an auscultation system including a first signal detector and a network interface. The first signal detector is configured to detect biosignals including infrasonic and audible signals from a body of a patient. The first signal detector includes a body and a first earbud coupled to the body. The first earbud includes an acoustic sensor that is configured to detect the biosignals from the body of the patient, via the body of the first signal detector. The network interface is configured to forward the biosignals from the first signal detector.

Preferably, the system additionally includes a remote device and a data analysis system. The remote device includes an application programming interface (API) configured to receive the biosignals forwarded from the network interface, and the data analysis system is configured to access the biosignals at the API. Typically, the remote device is a computing device such as a server.

In one embodiment of the auscultation system, the body of the first signal detector includes a base configured to be positioned against the body of the patient near one or both lungs of the patient, and the data analysis system is configured to classify pulmonary events based upon the biosignals in conjunction with lung sound models. In another embodiment, the base is configured to be positioned against the body of the patient near a heart of the patient, and the data analysis system is configured to determine a heartbeat and heart sounds of the patient based upon the biosignals in conjunction with heart sound models.

In other embodiments, the auscultation system includes a second earbud that is configured to detect biosignals including infrasonic and audible signals from the body of the patient. In one example, the second earbud is configured to be placed at an ear canal of the patient and is configured to detect the biosignals from the ear canal, and the network interface is configured to forward the biosignals from the second earbud.

In yet another embodiment, the auscultation system includes the second earbud placed in an ear canal of the patient and includes the first signal detector. The network interface is configured to forward the biosignals from the second earbud and from the first signal detector. The base of the first signal detector is configured to be positioned against the body of the patient near an artery of the patient, and the data analysis system is configured to determine a level of arterial and/or valvular stenosis based upon the biosignals.

In still other embodiments, the auscultation system includes a second signal detector. The second signal detector includes a body with a base, and the second earbud is coupled to the body of the second signal detector. The base of the second signal detector is configured to be positioned against the body of the patient, and the second signal detector is configured to send the biosignals to the network interface. For example, in one of these embodiments, the first signal detector and the second signal detector are configured to be positioned in a substantially collinear fashion at a distance apart from one another and their bases are configured to be positioned against the body of the patient near a same blood vessel, and the data analysis system is configured to determine a pulse velocity of the patient based upon the biosignals.

In another exemplary embodiment, the first signal detector is disposed against the body of a pregnant patient near a heart of the patient, and the base of the second signal detector is disposed against the body of the patient near where a fetus of the patient resides, and the data analysis system is configured to isolate a heartbeat of the patient and a heartbeat of the fetus based upon the biosignals.

Preferably, the body of each of the signal detectors includes a membrane that is configured to enable the coupling of its earbud to its body, to provide an acoustic seal between its earbud and the body, and to enable removable attachment of its earbud from the body. In one implementation, the first signal detector includes at least one ECG sensor that is configured to detect biosignals including electrical biosignals from the body of the patient, and the network interface is configured to forward the electrical biosignals from the signal detector.

Additionally and/or alternatively, the first signal detector includes at least one ultrasound transducer that is configured to transmit ultrasound into and/or detect ultrasound reflected from the body of the patient, and the network interface is configured to forward the ultrasound biosignals from the first signal detector.

Typically, the first earbud is a wireless earbud, and the network interface is a wireless network interface of the first earbud. In another implementation, the first and the second earbuds are wireless, and the network interface is a wireless network interface of a controller board that receives the biosignals sent from the earbuds and then forwards the biosignals to the remote device.

In another implementation, the first earbud is a wireless earbud, and the network interface is a wireless network interface of the first earbud. In another implementation, the first and the second earbuds are wireless, and the network interface is a wireless network interface of a controller board that receives the biosignals sent from the earbuds and then forwards the biosignals to the remote device.

In another example, the first earbud includes at least one motion sensor that facilitates positioning and orientation of the first signal detector relative to the body of the patient.

In general, according to another aspect, the invention features a method for acquiring biosignals. The method comprises providing a first signal detector that detects biosignals including infrasonic and audible signals from a body of a patient, the first signal detector including a body including a base, and a first earbud coupled to the body. The first earbud includes an acoustic sensor that detects the biosignals from the body of the patient, via the body of the first signal detector. The method also comprises positioning the base against a body of a patient to receive biosignals, and forwarding the received biosignals toward a remote device across a network.

In one embodiment, the method further comprises positioning the base of the first signal detector against the body of the patient near a heart of the patient, accessing the biosignals at an application programming interface (API) presented by the remote device, and determining a heartbeat and heart sounds of the patient based upon the biosignals in conjunction with heart sound models.

In another embodiment, the method further comprises positioning the base of the first signal detector against the body of the patient near one or both lungs of the patient, accessing the biosignals at an application programming interface (API) presented by the remote device, and classifying pulmonary events based upon the biosignals in conjunction with lung sound models.

In other embodiments, the method further comprises positioning a second earbud at an ear canal of the patient that detects the biosignals including infrasonic and audible signals from the body of the patent in the ear canal, and forwarding the detected biosignals toward the remote device across the network.

In yet another embodiment, the method further comprises positioning the base of the first signal detector against the body of the patient near an artery of the patient, accessing the biosignals from the first signal detector and the second earbud at an application programming interface (API) presented by the remote device, and determining a level of arterial and/or valvular stenosis of the artery based upon the biosignals.

In still other embodiments, the method further comprises positioning a base of a body of a second signal detector against the body of the patient to receive biosignals, the second earbud being coupled to the body of the second signal detector, the second earbud detecting biosignals including infrasonic and audible signals from the body of the patient, and forwarding the biosignals received by the first and the second signal detectors toward the remote device across the network.

In one example, the method comprises positioning the first and the second signal detectors in a substantially collinear fashion at a distance apart from one another, with their bases disposed against the body of the patient near a same blood vessel, accessing the biosignals from the first and second signal detectors at the application programming interface (API) presented by the remote device, and determining a pulse velocity of the patient based upon the biosignals.

In another example, the method comprises positioning the base of the first signal detector against the body of a pregnant patient near a heart of the patient, positioning the base of the second signal detector against the body of the patient near where a fetus of the patient resides, accessing the biosignals from the first and second signal detectors at the application programming interface (API) presented by the remote device, and isolating a heartbeat of the patient and a heartbeat of the fetus based upon the biosignals.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 7A is a plot of heart sounds that include a murmur; FIG. 7B is a power spectrum plot of the heart sounds in FIG. 7A; FIG. 7C is a plot of heart sounds that do not include a murmur; and FIG. 7D is a power spectrum plot of the heart sounds in FIG. 7C;

FIG. 9 is a schematic diagram that shows another embodiment of the detection system, where the detection system includes a signal detector with a coupled earbud wired to the controller board as shown in FIG. 4, and where the signal detector also includes ECG sensors;

FIG. 10 and FIG. 11 are bottom and top views, respectively, of the signal detector in the detection system of FIG. 9;

FIG. 13A shows an echocardiogram; FIG. 13B shows a plot of cardiac signals obtained by a catheter; FIG. 13C shows a plot of cardiac biosignals obtained by the auscultation system; and FIG. 13D shows an electrocardiogram (ECG) signal;

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
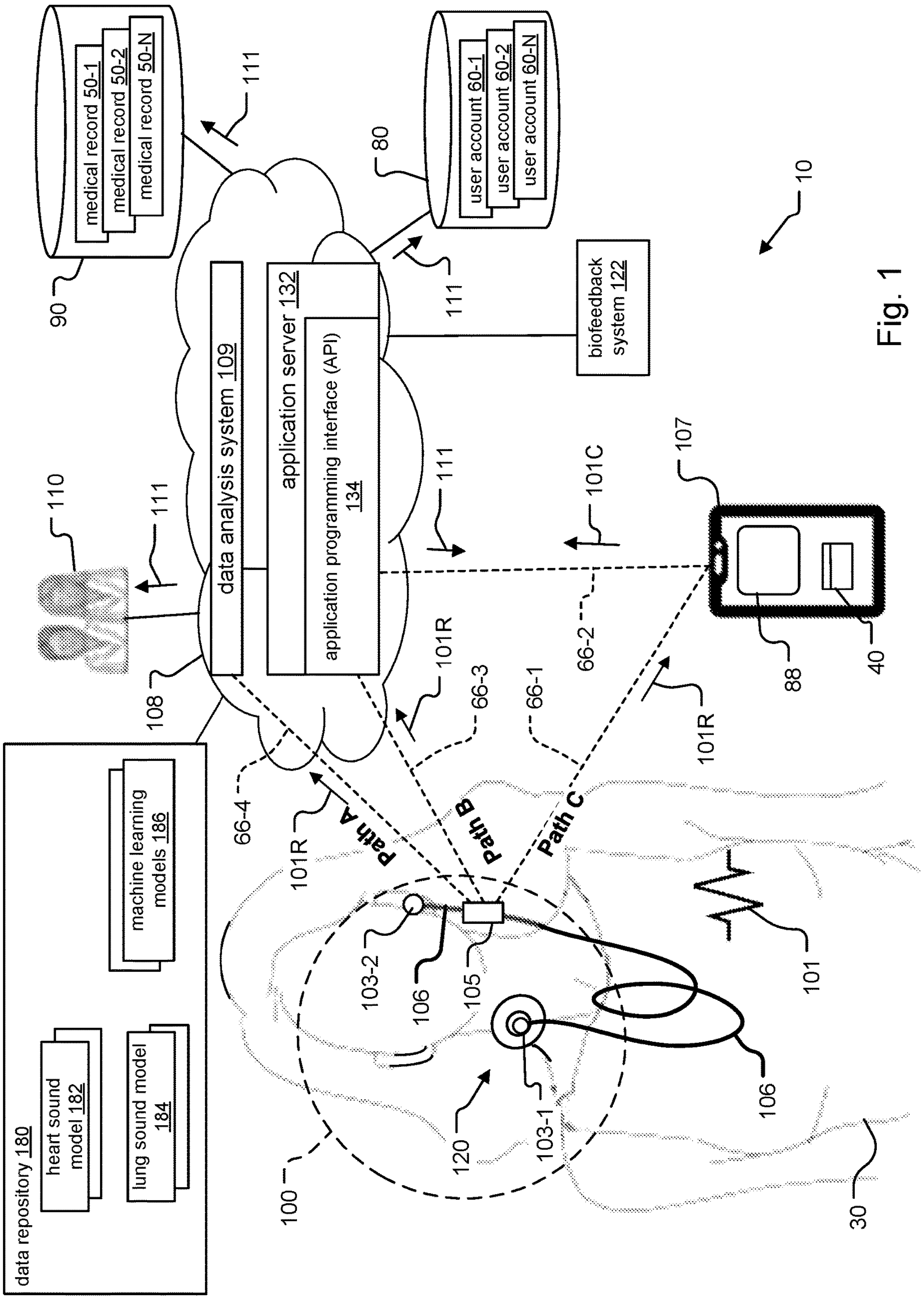
FIG. 1 is a schematic diagram of an exemplary earbud based auscultation system constructed in accordance with principles of the present invention, according to an embodiment, where the auscultation system includes an embodiment of a detection system worn by a patient.

FIG. 1 shows an exemplary earbud based auscultation system 10 constructed in accordance with principles of the present invention. The auscultation system 10 includes a detection system 100 worn by a patient 30, a data analysis system 109, a user device 107 carried by the patient 30 and various components within and/or in communication with a network cloud 108.

In one embodiment, as shown, the detection system 100 includes a signal detector 120 and a first earbud 103-1 coupled to the signal detector 120, a second earbud 103-2 and a controller board 105. The signal detector 120 is placed upon a body of the patient 30 (here, adjacent to the neck of the patient 30 near the right carotid artery) while the second earbud 103-2 is placed at an ear canal of the patient 30. In the illustrated example, the second earbud 103-2 is preferably placed in the ear canal on the side of the patient's body that opposes the location of the signal detector 120. Here, the auscultation system 10 is configured to operate in stenosis mode.

The earbuds 103 are in communication with and connect to the controller board 105 via an earbud connection 106. Here, the earbud connection 106 is a wired connection, but wireless connections are also supported. Typically, the controller board 105 is a separate component from the earbuds 103, but the controller board 105 can also be incorporated into one of the earbuds 103 or possibly into the signal detector 120, in examples.

The components of the auscultation system 10 that are either included within or in communication with the network cloud 108 include the data analysis system 109 and an application server 132, a medical record database 90, a user account database 80, a biofeedback system 122 and a data repository 180. The medical record database 90 includes medical records 50 of patients 30, while the user account database 80 includes user accounts 60 of patients 30 that are authorized users of the system 10.

A computing device includes at least one or more central processing units (CPUs) and a memory. The CPUs have internal logic circuits that perform arithmetic operations and execute machine code instructions of applications ("application code") loaded into the memory. The instructions control and communicate with input and output devices (I/O) such as displays, printers and network interfaces.

The CPUs of the computing devices are typically configured as either microprocessors or microcontrollers. A microprocessor generally includes only the CPU in a physical fabricated package, or "chip." Computer designers must connect the CPUs to external memory and I/O to make the microprocessors operational. Microcontrollers, in contrast, typically integrate the memory and the I/O within the same chip that houses the CPU.

The CPUs of the microcontrollers and microprocessors of the computing devices execute application code that extends the capabilities of the computing devices. In the microcontrollers, the application code is typically pre-loaded into the memory before startup and cannot be changed or replaced during run-time. In contrast, the CPUs of the microprocessors are typically configured to work with an operating system that enables different applications to execute at different times during run-time.

The operating system has different functions. The operating system enables application code of different applications to be loaded and executed at run-time. Specifically, the operating system can load the application code of different applications within the memory for execution by the CPU, and schedule the execution of the application code by the CPU. In addition, the operating system provides a set of programming interfaces of the CPU to the applications, known as application programming interfaces (APIs). The APIs allow the applications to access features of the CPU while also protecting the CPU. For this reason, the operating system is said to execute "on top of" the CPU. Other examples of CPUs include Digital Signal Processors (DSPs), Application Specific Integrated Circuits (ASICs), and Field Programmable Gate Arrays (FPGAs).

The user device 107 can be a portable or a stationary user device. In examples, portable user devices include mobile phones, smart glasses, smart watches, and laptops, in examples. The stationary user devices include workstations and gaming systems, in examples. A mobile phone/smartphone user device 107 carried by patient 30 is shown.

Each user device 107 is a computing device that includes a display 88 and one or more applications. An interactive user application running on each user device 107, or app 40, is shown. The app 40 of each user device 107 executes upon a CPU of the user device 107, receives information sent by other components in the system 10 and presents a graphical user interface (GUI) on the display 88. The GUI allows the patient 30, a medical professional or other individual with the patient 30 to enter information at the app 40 for configuring and operating the auscultation system 10 and presents various information upon the display 88.

The application server 132 is a computing device that connects client devices to components within or at the network cloud 108. The client devices include the controller board 105 and the user devices 107. The application server 132 includes secure website software (or a secure proprietary application) that executes on the application server 132. The application server 132 also includes or otherwise presents an application programming interface ("API") 134.

The data repository 180 includes various components. These components include heart sound models 182, lung sound models 184 and machine learning models 186. The data repository 180 can also include software programs that the data analysis system 109 and/or the app 40 can access at startup and/or during run-time.

Medical professionals 110 are also shown. The medical professionals 110 include doctors, nurses/nurse practitioners, physician's assistants, and medical technicians, in examples. The medical professionals 110 are trained in the use of the auscultation system 10. The medical professionals use computing devices such as laptops or smartphones to securely connect to the network cloud 108. In examples, the medical professionals 110 can connect to the network cloud 108 through telehealth services, or virtual clinics, with patient information provided by the auscultation system 10.

The medical professionals 110, the databases 80/90, the user devices 107, the biofeedback system 122 and the data repository 180 can connect to the network cloud 108 and/or components within the cloud 108 in various ways. These connections can be wired Internet-based or telephony connections, wireless cellular connections, and/or wireless Internet-based connections (e.g., Wi-Fi), in examples. In examples, the network cloud 108 can be a public network, such as the Internet, or a private network.

The controller board 105 and the user devices 107 communicate with each other and with the network cloud 108 via one or more wireless communications links 66. In more detail, the user device 107 connects to the controller board 105 via wireless link 66-1 and connects to the application server 132 via wireless link 66-2. The controller board 105 can also communicate with the application server 132 via wireless link 66-3 and might connect directly to the data analysis system 109 via wireless link 66-4. The wireless links 66 might be cellular-based or Internet-based (e.g., IEEE 802.11/Wi-Fi), or possibly even Bluetooth. In one example, the wireless links 66-3 and 66-4 are high-speed 5G cellular links. These links 66 are also encrypted to provide secure communications between the components that are at endpoints of the links 66.

In the illustrated example, the data analysis system 109 and the application server 132 are remote devices located in the network cloud 108. The network cloud 108 is remote to the patient 30. In this way, the application server 132 and the data analysis system 109 can service possibly thousands or more patients 30 wearing detection systems 100, where the patents can be in different geographically distributed locations. Alternatively, the data analysis system 109 and/or the application server 132 might also be located on a local area network within a premises, such as a residence, commercial building or place of business of the patient 30. In one implementation, the capabilities provided by the application server 132 are incorporated into the data analysis system 109.

The API 134 enables exchange of information between the clients of the auscultation system 10 and the network cloud 108. The API 134 also prevents the clients from accessing or modifying internal data, files and other resources of the components within the network cloud 108. For this purpose, the API 134 presents a set of public software interfaces which the clients can access. The public software interfaces, in turn, map to internal software and/or firmware functions and methods of the application server 132 that reference or otherwise access private data, files and other resources of the application server 132, the data analysis system 109, and/or other components of the network cloud 108.

In another implementation, the API 134 is included within the data analysis system 109. In this example, the clients of the system 10 are first authorized by the application server 132, and the application server forwards information sent by the authorized clients to the API 134 of the data analysis system 109.

Infrasound

Biosignals 101 such as acoustic signals are generated internally in the body by breathing, heartbeat, coughing, muscle movement, swallowing, chewing, body motion, sneezing and blood flow, in examples. The acoustic signals can be also generated by external sources, such as air conditioning systems, vehicle interiors, various industrial processes, etc. The acoustic signals include audible and infrasonic signals, and possibly ultrasound signals.

The acoustic signals represent fluctuating pressure changes superimposed on the normal ambient pressure of the patient's body and can be defined by their spectral frequency components. Sounds with frequencies ranging from 20 Hz to 20 kHz represent those typically heard by humans and are designated as falling within the audible range. Sounds with frequencies below the audible range (i.e., from 0 Hz to 20 Hz) are termed infrasonic or infrasound. The level of a sound is normally defined in terms of the magnitude of the pressure changes it represents. These changes can be measured and do not depend on the frequency of the sound.

The earbuds 103 each include at least one acoustic sensor that detects acoustic signals including audible biosignals and infrasonic biosignals from the body of the patient 30. The biologically-originating sound detected inside the ear canal by the first earbud 103-1 and detected within a cavity of the signal detector 120 by the second earbud 103-2 includes both infrasonic and audible signals.

Typically, the biosignals 101 are detected at each of the earbuds 103-1, 103-2 at substantially the same times. This "stereo effect" can be utilized to identify and address artifacts in the biosignals 101, as well as to improve a signal to noise ratio (SNR) of the biosignals 101 and thus provide high quality signals for subsequent characterization and analysis.

The auscultation system 10 generally operates as follows. A patient or other individual with the patient 30 enters credentials of the patient at the GUI of the app 40, which the user device 107 sends over link 66-2 to the application server 132. The application server 132 receives the credentials and verifies that the credentials are associated with an authorized patient user of the auscultation system 10. For this purpose, the secure website software at the application server 132 compares the received credentials to those stored within the user accounts 60 of the user account database 80. Upon finding a match, the application server 132 establishes an authenticated, secure login session over wireless connection 66-2 between the app 40 and the application server 132 for the patient 30 as an authorized user of the system 10.

After the login session is established, the application server 132 joins the controller board 105 and the data analysis system 109, in conjunction with the app 40, as part of a communications session. During the communications session, the patient 30 configures and operates the auscultation system 10 and its components via the app 40.

At the same time, the earbuds 103 continuously detect and collect the biosignals 101 from the patient 30 and send the biosignals 101 to the controller board 105. Here, the biosignals are in "raw" format: they are uncompressed and may include some noise and/or motion artifacts. In another embodiment, the biosignals 101 might also be compressed, filtered, and pre-analyzed. The controller board 105 buffers the biosignals 101 for subsequent secure transmission/forwarding to the interface 134.

Once the application server 132 indicates to the user device 107 that the patient 30 is an authorized user, the user device 107 can signal the controller board 105 to send the detected biosignals 101 to the interface 134 or to the data analysis system 109 by way of one or more communications paths. These paths are labeled Path A, B, and C in the figure. These paths respectively include zero, one, or more than one intermediary components or "hops" between the controller board 105 and the data analysis system 109. The decision of whether to send the biosignals 101 along the different paths depends on factors including the CPU speed of the components at the endpoints of the links 66, the buffer sizes of the wireless transceivers in the components that form each path, and characteristics of the wireless links 66 that form the communications paths. These characteristics include speed, level of encryption and available bandwidth, in examples. A description for each Path A, B and C follows hereinbelow.

Path C is typically the slowest communications path. This path includes wireless links 66-1 and 66-2, and includes the user device 107 and the interface 134 of the application server 132 as intermediary components between the controller board 105 and the data analysis system 109. In more detail, the controller board 105 first sends raw versions of the biosignals over link 66-1 to the user device 107, indicated by reference 101R. The app 40 then compresses the raw biosignals 101R into compressed versions of the biosignals 101C for transmission over link 66-2 to the interface 134.

In the illustrated example, the API 134 of the application server 132 receives the compressed biosignals 101C from the user device 107. The application server 132 then decompresses the compressed biosignals 101C, and the data analysis system 109 can access the (uncompressed) biosignals 101 at/via the interface 134. The API 134 can also act as an intermediary for any signals or messages sent between the data analysis system 109 and the client devices (e.g., the controller board 105 and the user device 107). The data analysis system 109 can then access the biosignals 101 at the interface 134.

Path B is generally faster than Path C. Path B includes wireless link 66-3 and only one intermediary component, the application server 132, between the controller board 105 and the data analysis system 109. Because link 66-3 is a fast or high throughput link (such as a 5G cellular link), the controller board 105 can send the raw biosignals 101R over link 66-3 to the application server 132/API 134 without having to compress the signals prior to transmission.

The application server 132/API 134 can perform various operations on the raw biosignals 101R before making the biosignals available for the data analysis system 109 to access and then analyze. These operations include filtering and characterization, authentication, and/or buffering of the signals. As with Path C, the API 134 can also act as an intermediary for any signals or messages sent between the data analysis system 109 and the controller board 105. The data analysis system 109 can then access the biosignals 101 at the interface 134.

Path A is typically the fastest path because it utilizes direct link 66-4 from the controller board 105 to the data analysis system 109. As a result, the controller board 105 can send the raw biosignals 101R directly to the data analysis system 109 over link 66-4. As noted herein above, the data analysis system 109 might also include an API 134 that operates as a communications intermediary or a buffer between the controller board 105 and the data analysis system 109.

The data analysis system 109 analyzes the biosignals 101 and can use information from the data repository 180 during the analysis. In one example, the data analysis system 109 can use the heart sound models 182 when detecting and characterizing heart sounds. The data analysis system 109 and/or the application server 132 can access and update the medical record 50 of the patient 30 during and in response to the analysis. Any data such as infrasounds obtained by the detection system 100 for each patient is stored as a time-stamped entry in the medical record 50 for each patient 30.

The data analysis system 109 can also send various notification messages 111 in response to the analysis of the biosignals 101. The notification messages 111 include information concerning the analysis and the results of the analysis. The messages 111 can be sent to the medical professionals 110, the databases 80/90, the user devices 107, and possibly even the controller board 105. The notification messages 111 can be in the form of an email, SMS/text message, phone call, database record in proprietary format or XML or CSV format, or possibly even audible speech, in examples.

The data analysis system 109 can also notify the patient 30 both during and after the analysis via the notification messages 111. In one example, the app 40 receives the notification messages 111 and might present the notification messages 111 at the display 88, or forward the messages 111 over the wireless link 66-1 to the controller board 105. At the controller board 105, the messages 111 might be in the form of audible sound messages for subsequent audio presentation at speakers included within the earbuds 103.

In this way, the auscultation system 10 can continuously monitor and analyze biosignals 101 including infrasound signals detected by and sent from detection systems 100 worn by different patients 30, and identify and characterize aspects of the biosignals 101. The system 10 can also update medical records 50 for each of the patients 30, report problems/notify medical professionals 110 of likely medical issues found during the analysis, and provide feedback to the patients 30 during and upon completion of the analysis.

Figure 2A:
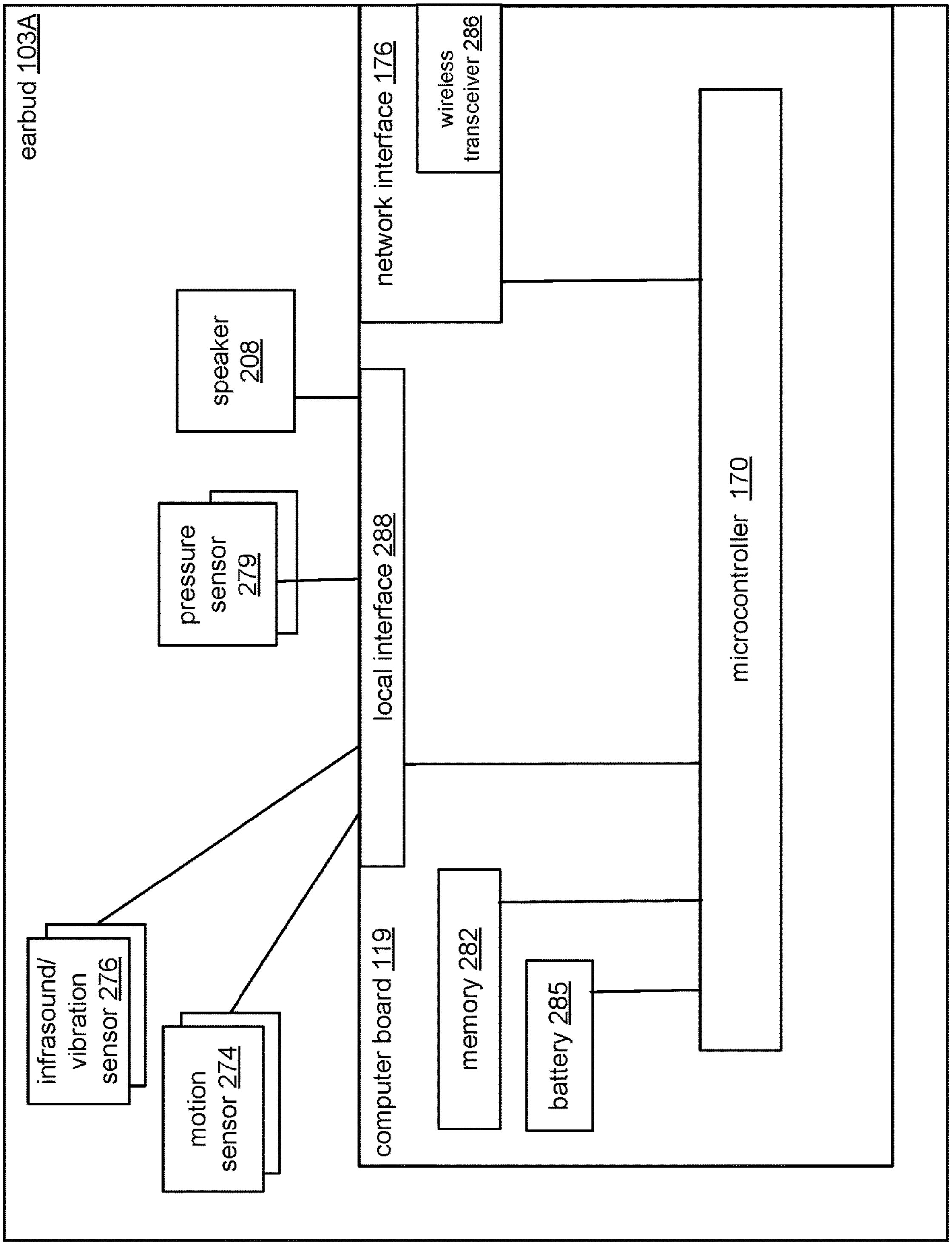
FIGS. 2A and 2B are block diagrams of exemplary earbuds in FIG. 1, where the diagrams shows components of the earbuds and connections between the components.

FIG. 2A is a block diagram of an exemplary earbud 103A that can be included in the auscultation system 10 of FIG. 1. The diagram shows components of the earbud 103A and connections between its components. In the illustrated example, the earbud 103A includes various sensors and a computer board 119. In more detail, the sensors include one or more motion sensors 274, one or more acoustic sensors such as infrasound/vibration sensors 276, one or more speakers 208 and one or more pressure sensors 279. The motion sensors include accelerometers and gyroscopes, in examples.

The infrasonic/vibration sensors 276 operate in the infrasonic range and might also operate in the audible range. In another example, two or more acoustic sensors in each earbud can detect sound in different frequency ranges (e.g., one for detecting infrasounds and the other for detecting audible sounds). Generally, the pressure sensors 279 detect constant or slow-changing pressures, whereas the acoustic sensors 276 measure pressure fluctuations over a much larger frequency range, e.g., from 0 Hz to 20 kHz and possibly larger.

The pressure sensors 279 serve multiple purposes. In one example, the pressure sensors 279 can be used to characterize a level of seal/occlusion of each earbud 103A with respect to an acoustic volume. The acoustic volume is within a cavity, where the cavity is either an inner ear canal of the patient 30 when the earbud 103A is placed at the inner ear canal of the patient 30, or an internal chamber of the signal detector 120 to which the earbud 103A is coupled when the signal detector 120 is disposed against the body of the patient 30. In another example, the sensors 279 can be used to monitor changes in baseline pressure in the cavities due to, for example, physiological changes.

The computer board 119 has a local interface 288 and includes earbud memory 282, a battery 285, a network interface 176 and a microcontroller 170. The network interface 176 includes a wireless transceiver 286. The sensors 274, 276, 279 and the speakers 208 connect to the computer board 119 via the local interface 288. The computer board 119 provides power to each earbud 103A/signal detector 120 and enables communications between each earbud 103A and components external to the earbud via the network interface 176.

The sensors 274, 276, 279 detect various information including sounds and vibrations, motion and pressure originating from the patient 30 and send biosignals 101 representing the information to the controller board 105. In one example, the sounds and vibrations are in the infrasonic range. These infrasounds and vibrations are typically associated with operation of the patient's heart and its various chambers and valves, and can also be associated with other cardiovascular components such as the lungs, arteries, veins, coronary and portal vessels. Additionally, the sounds from the patient 30 can be in the audible frequency range. These sounds can include those associated with breathing and snoring, in examples.

The motion sensors 274 detect movement of the patient (e.g., moving, sneezing, eye and head movements, arm and leg movements), and can thus facilitate positioning of the earbuds and/or the signal detectors of the auscultation system 10 at desired location and orientations relative to the body of the patient 30. For this purpose, the motion sensors 274 represent the motion as motion artifacts within the biosignals 101. The pressure sensors 279 detect pressure within cavities within which the earbuds 103A are placed and represent the pressure as pressure signals within the biosignals 101.

The computer board 119 also receives information from other components in the auscultation system 10 via the network interface 176. This information includes the notification messages 111 for presentation at the earbuds 103A, and commands sent from the app 40. In another example, the information includes updates for application code running within the microcontroller 170.

Figure 2B:
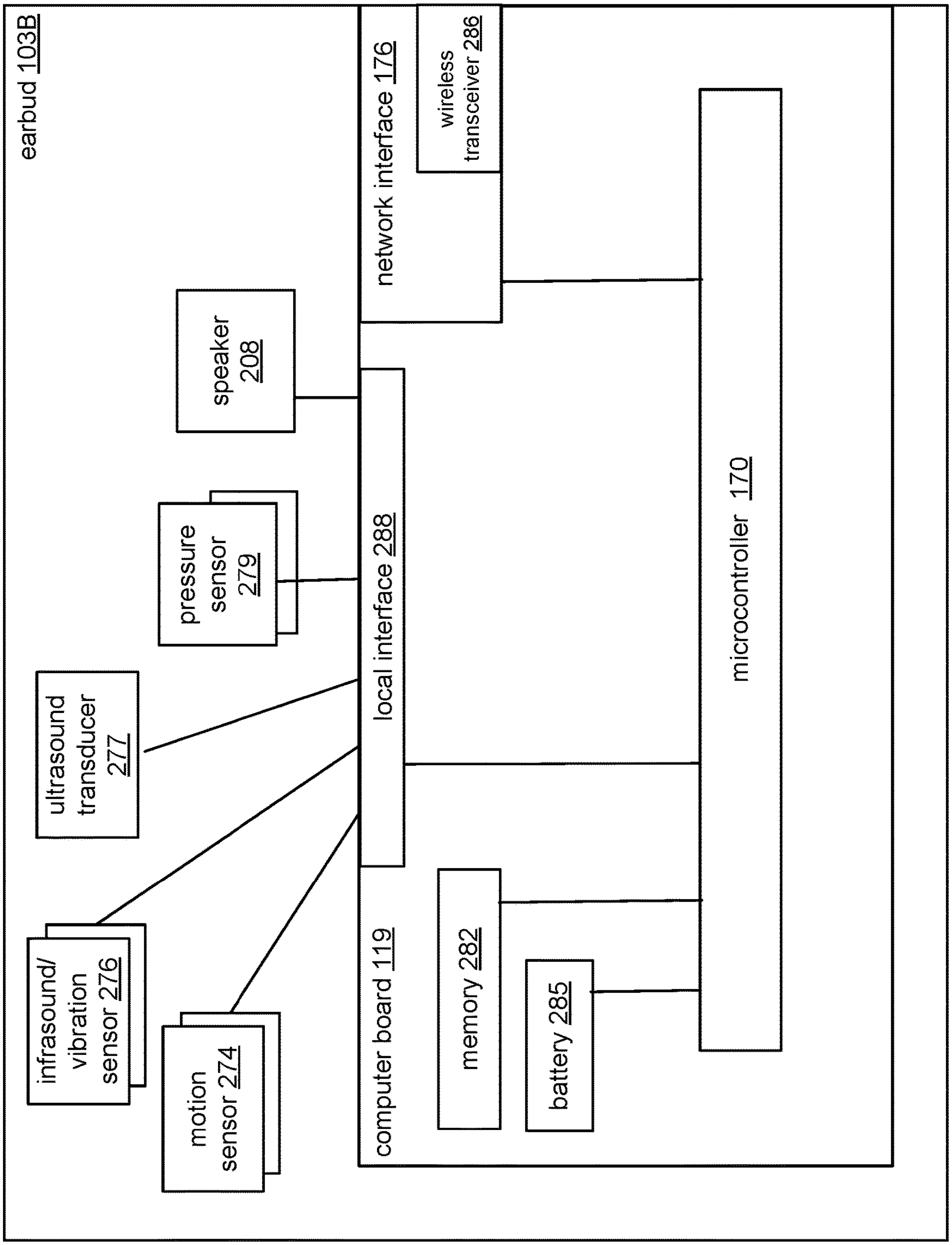

FIG. 2B is a block diagram of an earbud 103B that can be included in the auscultation system 10 of FIG. 1, according to another embodiment. The earbud 103B includes all components shown in and operates in a substantially similar manner as the earbud 103A of FIG. 2A. However, there are differences. The earbud 103B additionally includes at least one ultrasound transducer 277 that can transmit ultrasound into the body of the patient 30 and also detect ultrasound from the body of the patient 30. The ultrasound transducer 277 connects to the local interface 288.

More detail for the ultrasound transducer 277 is as follows. Its frequency range is typically in the range of 1 Megahertz (MHz) to 15 MHz. In other examples, this range can be from 20 kilohertz (KHz) to 1 MHz, 30 KHz to 15 MHz, or possibly from 30 kHz to 20 MHz, or ultrasounds greater than 20 MHz. The transducer 277 can operate as a sensor only to detect ultrasound, or can also operate as a transmitter and a sensor. In this embodiment, the earbud 103B can be used with a dry or wet couplant to minimize attenuation of ultrasound.

The earbud 103B has advantages. Via its various sensors/transducers, the earbud can detect frequencies in a range from 0 Hz to as much as 20 MHz or greater, which covers a wide acoustic spectrum that includes infrasound, audible sound and diagnostic ultrasound, while also providing "selective" sensing of specific frequency subranges tailored to specific tasks.

In general, higher ultrasound frequencies have shorter wavelengths and provide improved detail and spatial resolution. However, the higher ultrasound frequencies are easily absorbed by body tissue and thus are not as penetrating as lower frequency ultrasound. Traditional diagnostic ultrasound applications include hemodynamics and imaging of blood flow in different chambers of the heart. In examples, ultrasound with a center frequency of about 2.5 MHz is typically used for deep abdomen and gynecologic imaging; ultrasound with a center frequency of about 7.5 MHz is often used for thyroid and breast imaging; and ultrasound with a center frequency of about 15 MHz is typically used for musculoskeletal imaging.

Figure 3:
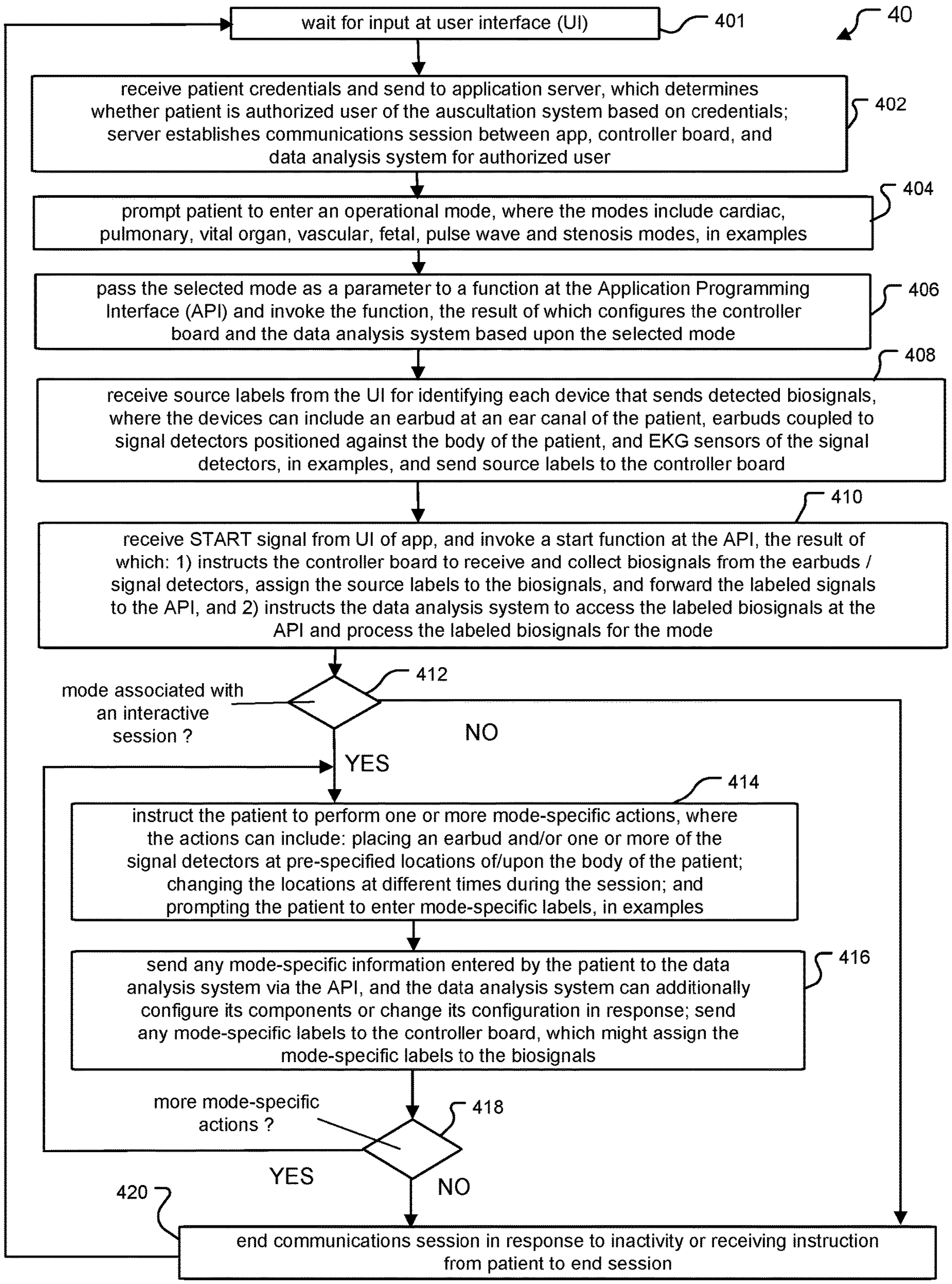
FIG. 3 is a flowchart that describes a method of operation of an application ("app") for configuring and operating the auscultation system, where the app executes on a user device carried by the patient, and where the patient or other individual with the patient can configure and operate the auscultation system via the app.

FIG. 3 is a flowchart that describes a method of operation of the app 40 in FIG. 1. Here, a patient 30 or other individual with the patient 30 configures the auscultation system 10 for different modes of operation via the app 40. In the method steps below, the patient 30 or another individual may interact with the app 40. The other individual might be a medical professional 110, or a layperson trained in operation of the auscultation system 10. The method begins at step 401.

In step 401, the app 40 waits for input from a patient 30 via a user interface (UI) of the app 40. In response to detecting input or other action, the method transitions to step 402. According to step 402, the app 40 receives credentials such as a username and password for the patient 30 and sends the credentials to the application server 132. The application server 132 determines whether the patient is an authorized user of the auscultation system 10 based on the credentials, and establishes a communications session between the app 40, the controller board 105 and the data analysis system 109 for the patient as an authorized user.

In step 404, the app 40 prompts the patient 30 to enter an operational mode. The operational mode can include cardiac, pulmonary, vital organ, vascular, fetal, pulse wave and stenosis modes, in examples. User defined-modes are also possible. Additionally and/or alternatively, modes directed to standard auscultation maneuvers for detecting cardiac murmurs are also possible.

Then, in step 406, the app 40 passes the selected mode as a parameter to a function at the application programming interface (API) 134 and invokes the function, the result of which configures the controller board and the data analysis system 109 based upon the selected mode. This configuration step can include the models 182, 184, 186 or other datasets.

According to step 408, the app 40 receives source labels entered by the patient 30 at the UI of the app 40. The patient 30 enters the source labels to identify the devices of the auscultation system that the patient is using to detect the patient's biosignals 101. In examples, the devices can include an earbud 103 at an ear canal of the patient 30, earbuds 103 coupled to signal detectors 120 disposed against the body of the patient, and EKG sensors included within signal detectors, in examples. The app 40 sends the source labels to the controller board 105.

In more detail, the patient 30 is prompted at the app 40 to enter source labels that the data analysis system 109 (and possibly other components) can further use to configure and operate the auscultation system 10. For this purpose, in one example, the earbuds 103 and/or the signal detectors 120 may be preconfigured with different numbers affixed thereon. After the patient enters the mode, the app 40 might ask the patient 30 to enter the number affixed to each device, and instruct the patient 30 to place the earbud 103 or signal detector at/upon a specific body location in accordance with the selected mode. The app 40 then assigns a predetermined source label for each of the devices in response.

In another example, the app 40 might send signals to the controller board 105 that instruct the controller board 105 to sequentially send an audible tone to each of the earbuds 103. After the patient 30 hears the tone at an earbud 103, the patient can then enter one or more associated source labels at the app 40 that indicate a location of the body upon/at which the patient has placed or intends to place each device (e.g., an earbud 103, or a signal detector 120 that includes an earbud 103 coupled to the signal detector 120). The app 40 then includes or otherwise maps information that identifies each of the earbuds 103/signal detectors 120, such as a unique hardware address, with each source label.

The app 40 sends the source labels to the controller board 105. The controller board 105 continuously receives biosignals 101 from the earbuds 103 and/or signal detectors 120, collects/buffers the biosignals 101 into different sets of biosignals, and assigns the source labels and the mode label(s) to the set(s) of biosignals 101. In this way, other components of the system 10 such as the data analysis system 109 can access the labels (e.g., source labels, or other labels) assigned to each set of biosignals 101 to identify which device detected and sent the biosignals 101. When labels are assigned to the biosignals 101, the biosignals are also known as labeled biosignals.

In step 410, the app 40 receives a START signal entered by the patient 30 at the UI. The app 40 invokes a START interface function in response, the result of which: 1) instructs the controller board 105 to receive and collect biosignals from the earbuds/signal detectors, assign the source labels to the biosignals, and forward the labeled signals to the API 134; and 2) instructs the data analysis system 109 to access the labeled biosignals at the API 134, and to process the labeled biosignals 101 for the selected mode.

If the data analysis system 109 determines that the mode/mode label is associated with an interactive patient session in step 412, the method transitions to step 414. Otherwise, the method transitions to step 420.

At step 414, the app 40 is engaged in an interactive session with the patient 30, the controller board 105 and the data analysis system 109. In such a session, the app 40 can instruct the patient to perform one or more mode-specific actions. These can include instructing the patient 30 to place an earbud and/or one or more of the signal detectors 120 at pre-specified locations of/upon the body of the patient 30, to change the locations of these devices at different times during the session, and to enter mode-specific information including body locations where the signal detectors are placed and to enter mode-specific labels, in examples. At step 416, the app 40 sends any mode-specific information entered by the patient 30 during the interactive session to the data analysis system 109 via the API 134, where the data analysis system 109 can additionally configure its components/change its configuration in response. The app 40 also sends any mode-specific information to the controller board 105, which might assign the mode-specific labels to the biosignals 101.

The controller board 105 might assign the labels to the biosignals 101 as follows. In one example, the controller board 105 can prepare data messages for use with different standard or proprietary communications protocols, include the biosignals 101 as payload of the messages, include the labels in the messages (either in payload or message headers/metadata), and send the messages to the API 134. Components of the system 10 can configure the system based upon the labels, enter an operational mode based upon the labels, or otherwise change their behavior based upon the labels, in examples. In another example, the sets of biosignals 101 are included in communications packets, and the controller board 105 assigns the labels to metadata of the communications packets.

In step 418, the app 40 determines if there are any more mode-specific actions to process. If so, the method transitions back to the beginning of step 414 to perform the next mode-specific action; otherwise, the method transitions to step 420. At step 420, the app 40 ends the communication session in response to inactivity or after receiving an instruction from the patient to end the session (i.e., STOP command, session logout). Upon completion of step 420, the method transitions back to step 401 to await a new interaction from the patient 30.

It is also important to note that the data analysis system 109 is typically configured to concurrently process biosignals 101 obtained by and sent from detection systems 100 worn by different patients 30. For this purpose, in one example, the data analysis system 109 might create a separate process that executes across one or more processing nodes/processors of the data analysis system 109 for each patient 30. The data analysis system 109 then presents the processes as separate, virtualized instances of the data analysis system 109 to each patient 30. When each patient 30 at the app 40 establishes a communications session with the controller board 105 of each detector system 100, the application server 132 and the data analysis system 109, the patient 30 is thus communicating with the separate virtualized instance of the data analysis system 109 for that patient 30. In this way, each patient 30 or other individual can configure and operate the auscultation system 10 for their independent use.

It can also be appreciated that when the patient 30 is engaged in an interactive communications session with the system 10, the data analysis system 109, application server 132 or other component might send a list of instructions to the app 40 for the patient 30 to perform during each mode. These instructions might include instructing the patient 30 to move one or more signal detectors 120 to different locations of or near the patient's body at different times, instructing the patient 30 to place the second earbud at a different ear canal or to remove it from the ear canal altogether, and instructing the patient to exhale or move parts of their body during the session, in examples. These instructions are typically tailored to the current operational mode of the auscultation system 10.

During each mode, the data analysis system 109 can also request information and other input from the patient 30. In one example, the data analysis system 109 might require the patient 30 to enter an "OK" at the app 40 after each change in location of the signal detector 120 or second earbud 103-2. This enables the data analysis system 109 to operate more efficiently. In another example, at the start of a session, the data analysis system 109 might access the medical record 50 of the patient 30 and send a list of known prescription medications and medical history to the patient 30 via the app 40. The patient 30 confirms or updates this information in response, and can also enter information regarding their current state. This information can include whether the patient 30 has taken necessary prescription medications such as insulin or heart medicine, or is experiencing a health issue such as dizziness, chest pain or shortness of breath, in examples.

In yet another example, the data analysis system 109 might prompt the patient 30 via the app 40 to enter one or more labels (e.g., mode, source, and mode-specific labels) at different times during each session. Components of the system 10 can then use the labels to configure the system, or to associate the labels with the biosignals 101 to provide information regarding which signal detector 120 or earbud 103 detected the biosignals 101, the placement locations of the signal detectors, and possibly other information. The data analysis system 109 can then customize the processing/analysis of the biosignals 101 using different algorithms, machine learning models 186, or the like, based upon the labels/in an associated context indicated by the labels.

In yet another example, a medical professional 110 might be able to join the interactive session and help direct the patient 30 during the session. For this purpose, the interactive session might be an interactive audiovisual communications session, where the medical professional 110 can guide the patient 30 through different steps (or repeat steps as necessary). Additionally and/or alternatively, the medical professional 110 can change the configuration of the data analysis system 109, possibly in real time, based upon clinical and diagnostic objectives, in response to changes in physiological state(s) of the patient 30 that the patient has reported, and/or in response to changes in physiological state(s) of the patient 30 that the data analysis system 109 has determined upon analyzing the biosignals 101, in examples.

In still other examples, the earbuds might each "stamp" the detected biosignals with an identifier or label, or otherwise include a unique identifier for each earbud in messages sent to the API 134 that include the biosignals. In this way, when the earbuds 103 and/or the signal detectors 120 send the biosignals to the API 134, third party applications or other components that access the biosignals at the API 134, such as the data analysis system 109, can identify the source of the biosignals 101.

The auscultation system 10 also supports standard auscultation maneuvers for detecting cardiac murmurs. These maneuvers include: a Valsalva maneuver; respiration (both upon inhale and exhale); squatting from a standing position and standing from a squatting position; leg raising and handgrip exercise, in examples. Via the app 40, the patient 30 or other individual can configure the auscultation system 10 for each of the maneuvers.

Figure 4:
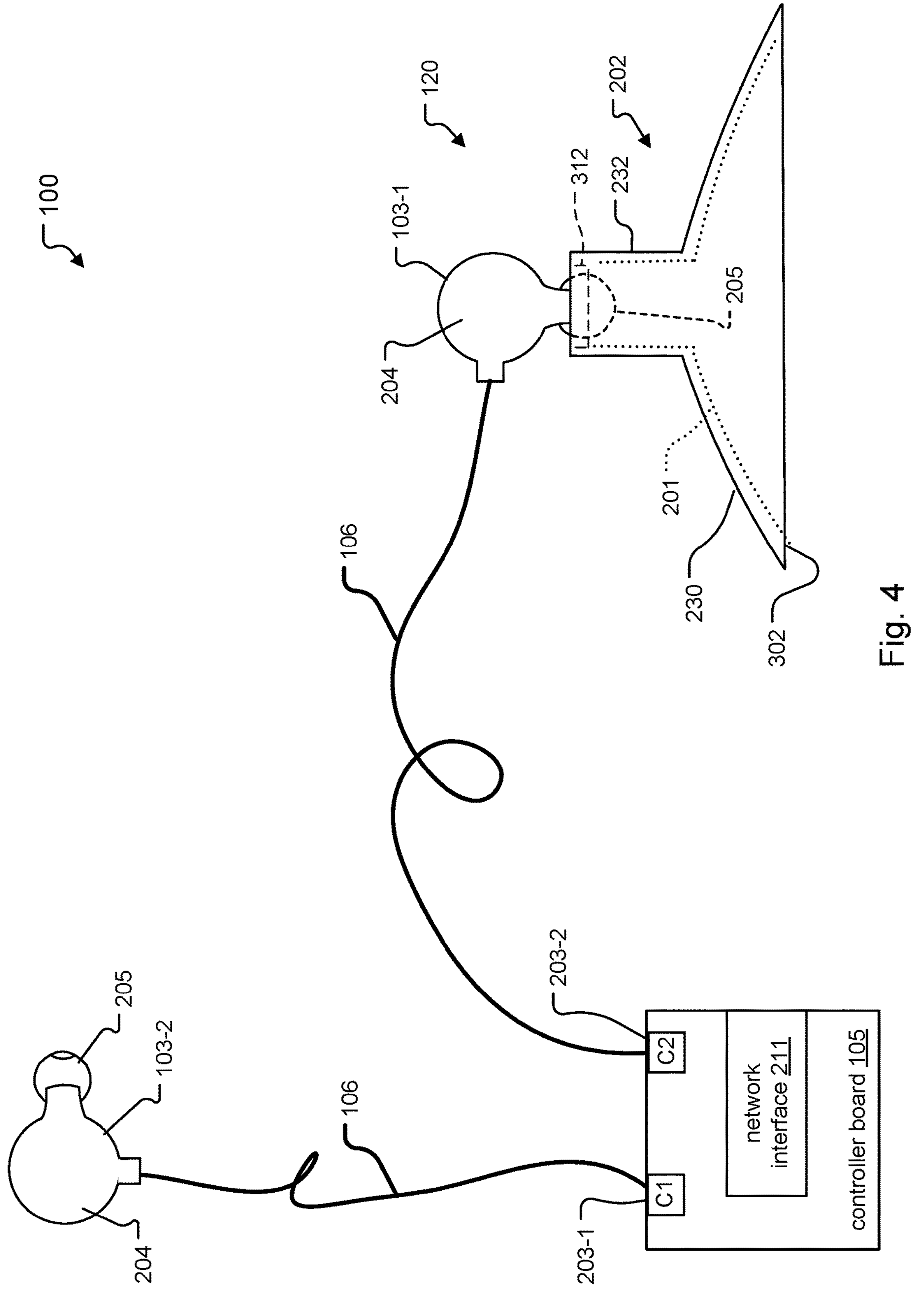
FIG. 4 is a schematic diagram that shows more detail for the detection system in FIG. 1, where the detection system includes a controller board, a signal detector with a first earbud coupled to a body of the signal detector, and a second earbud for placement at an ear canal of the patient, and where the first and second earbuds have a wired connection to the controller board.

FIG. 4 shows more detail for the detector system 100 in FIG. 1. The signal detector 120 has a body 202 with a base 230 and a vertical member 232 that rises upward from the base 230. A bottom 302 of the base 230 faces and is positioned against the body of the patient 30. The first earbud 103-1 is coupled to the body 202. Typically, a couplant such as a dry or gel couplant is added to the skin of the patient's body and sits between the body and the bottom 302 of the base 230 when the signal detector 120 is placed against the body of the patient 30.

The earbuds 103-1, 103-2 each have an earbud housing 204 and an earbud tip 205 that attaches to the earbud housing 204. The second earbud 103-2 is inserted at the ear canal of the patient 30. The controller board 105 has two channels 203-1 and 203-2, also labeled as C1 and C2, respectively. A network interface 211 of the controller board 105 is also shown.

These components are arranged as follows. The second earbud 103-2 has a wired earbud connection 106 from its earbud housing 204 to channel C1 of the controller board 105. The patient 30 places the earbud tip 205 of the second earbud 103-2 at an ear canal of the patient 30 during operation of the auscultation system 10. The first earbud 103-1 has a wired earbud connection 106 from its earbud housing 204 to channel C2 of the controller board 105.

The first earbud 103-1 is coupled to the body 202 as follows. The vertical member 232 includes a membrane 312 (shown in phantom) that accepts an earbud 103. The first earbud's earbud tip 205 (also shown in phantom) is removably and sealably attached to the membrane 312. When the first earbud 103-1 is coupled to the body 202 of the signal detector 120 as shown, the earbud tip 205 seats within a cavity 201 of the body 202. This cavity is enclosed by the inside surface of the body 202 and the body of the patient 30 when the bottom 302 of the base 230 is placed against the body of the patient 30.

The network interface 211 of the controller board 105 collects and buffers the biosignals 101 received from the earbuds 103-1, 103-2 over the channels C1 and C2, and forwards the biosignals 101 to a remote device such as the application server 132.

Figure 5:
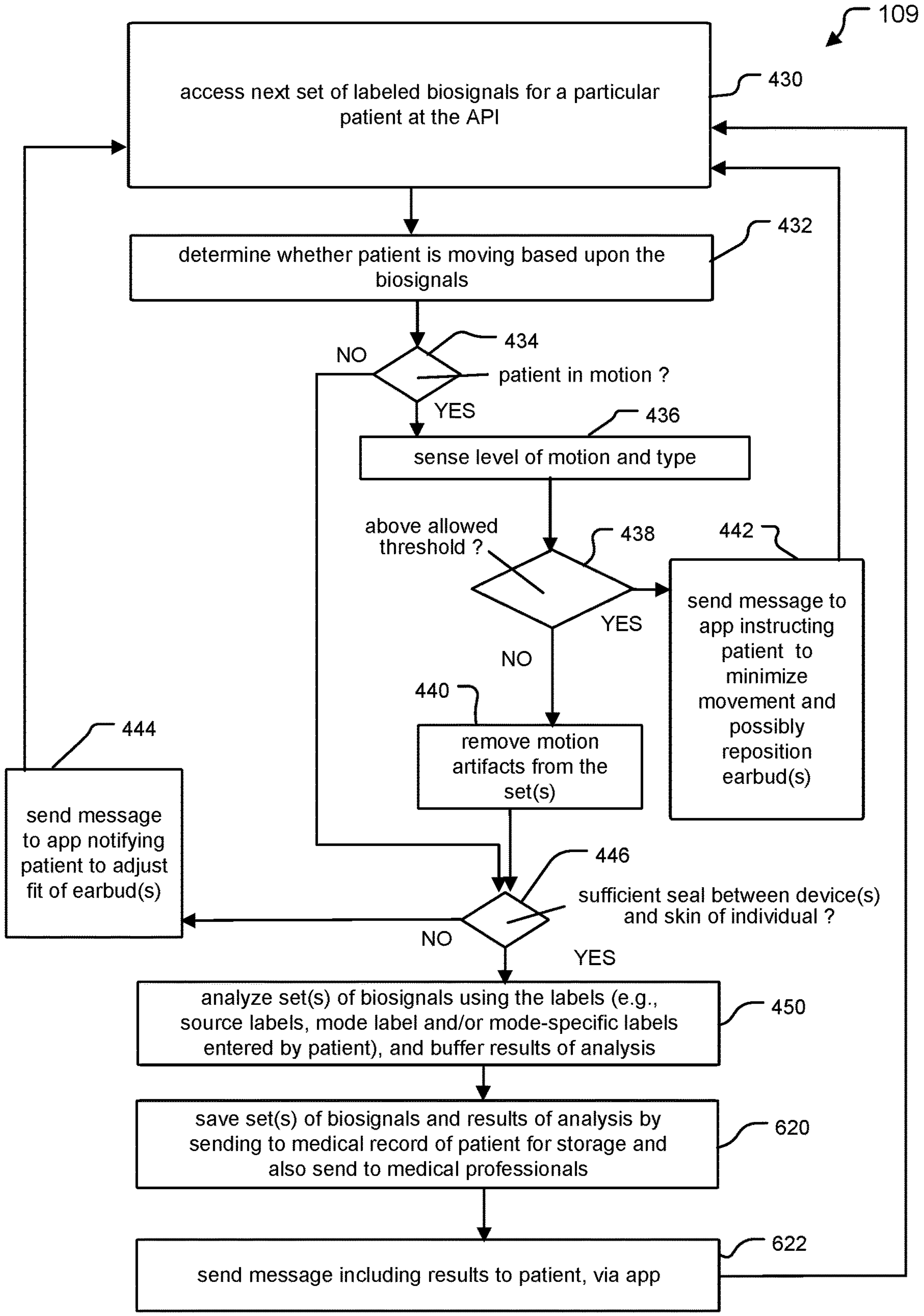
FIG. 5 is a flowchart that describes a method of operation of a data analysis system in the auscultation system, where the method describes how the data analysis system analyzes biosignals from the body of a patient detected by and sent from the detector system, configures the auscultation system into different modes of operation and reports results of the analysis.

FIG. 5 is a flowchart that describes a method of operation of the data analysis system 109. At step 430, the data analysis system 109 accesses a next set of labeled acoustic biosignals 101 for a particular patient at the API 134. In step 432, the data analysis system 109 determines whether the patient 30 is moving based upon the biosignals 101. If the data analysis system 109 in step 434 determines that the patient is moving, the method transitions to step 436; otherwise, the method transitions to step 446.

In step 436, the data analysis system 109 senses a level and a type of the motion. If the level of the motion is above a maximum allowed threshold value, the method transitions to step 442 to cease processing of the biosignals 101; otherwise, the method transitions to step 440. Additionally and/or alternatively, the data analysis system 109 might analyze the detected motion associated with the biosignals from each earbud/signal detector, with or without the associated biosignals 101, and perform other tasks based upon the analysis. More detail for these tasks can be found following the description of FIG. 20, included herein below.

In step 442, the data analysis system 109 sends a message to the app 40 instructing the patient 30 to minimize movement and possibly reposition the earbuds 103 of the detector system 100 or the signal detectors 120 relative to the body of the patient 30. The earbud repositioning can include repositioning an earbud placed at the patient's ear and/or repositioning earbud(s) coupled to the signal detectors 120, in examples. Upon conclusion of step 442, the method transitions back to step 430 to access the next set of labeled biosignals 101.

At step 440, because the level of motion within/associated with the biosignals 101 was determined to be at an acceptable level, the data analysis system 109 continues processing of the biosignals 101 by removing artifacts associated with the motion from the set or sets(s) of biosignals 101. Additionally and/or alternatively, the data analysis system 109 might analyze the detected motion associated with the biosignals from each earbud/signal detector, with or without the associated biosignals 101, and perform other tasks based upon the analysis. More detail for these tasks can be found following the description of FIG. 20, included herein below. The method then transitions to step 446.

At step 446, the data analysis system 109 determines whether a sufficient seal exists for each of the earbuds 103. For this purpose, in one example, the pressure sensor 279 for an earbud 103 reports a pressure detected around the earbud/in a cavity within which the earbud is inserted. The cavity can be the inner ear canal of the patient 30 when a second earbud 103-2 is placed at the inner ear of the patient 30 or can be a hollow interior of a signal detector 120 when the first earbud 103-1 is coupled to the signal detector 120, in examples.

When the data analysis system 109 determines that the seal for an earbud 103 is insufficient, the data analysis system 109 stops processing the current set of biosignals 101 and transitions to step 444. At step 444, the data analysis system 109 sends a message to the app 40 to notify the patient to adjust the fit of earbud(s), either at their ear canal or within the signal detectors, and control returns to step 430 to access the next set of labeled biosignals 101 at the API 134. Otherwise, because the seal at each of the earbud(s) 103 is sufficient, the method transitions to step 450.

At step 450, the data analysis system 109 analyzes the set(s) of labeled biosignals using the labels (e.g., source labels, mode label and/or mode-specific labels entered by patient 30), and buffers the results of the analysis. In one example, based upon the mode label and/or mode-specific labels, the data analysis system 109 can configure its components and other components of the auscultation system 10 for mode-specific operation.

In step 620, the data analysis system saves the set(s) of biosignals 101 and the results of analysis by sending them to the medical record 50 of the patient 30 for storage. The data analysis system 109 might also send this information to one or more medical professionals 110. At step 622, the data analysis system 109 also sends a message including the results to the patient 30 via the app 40. The method then transitions back to step 430 to access the next set of biosignals 101 from the API 134.

Figure 6:
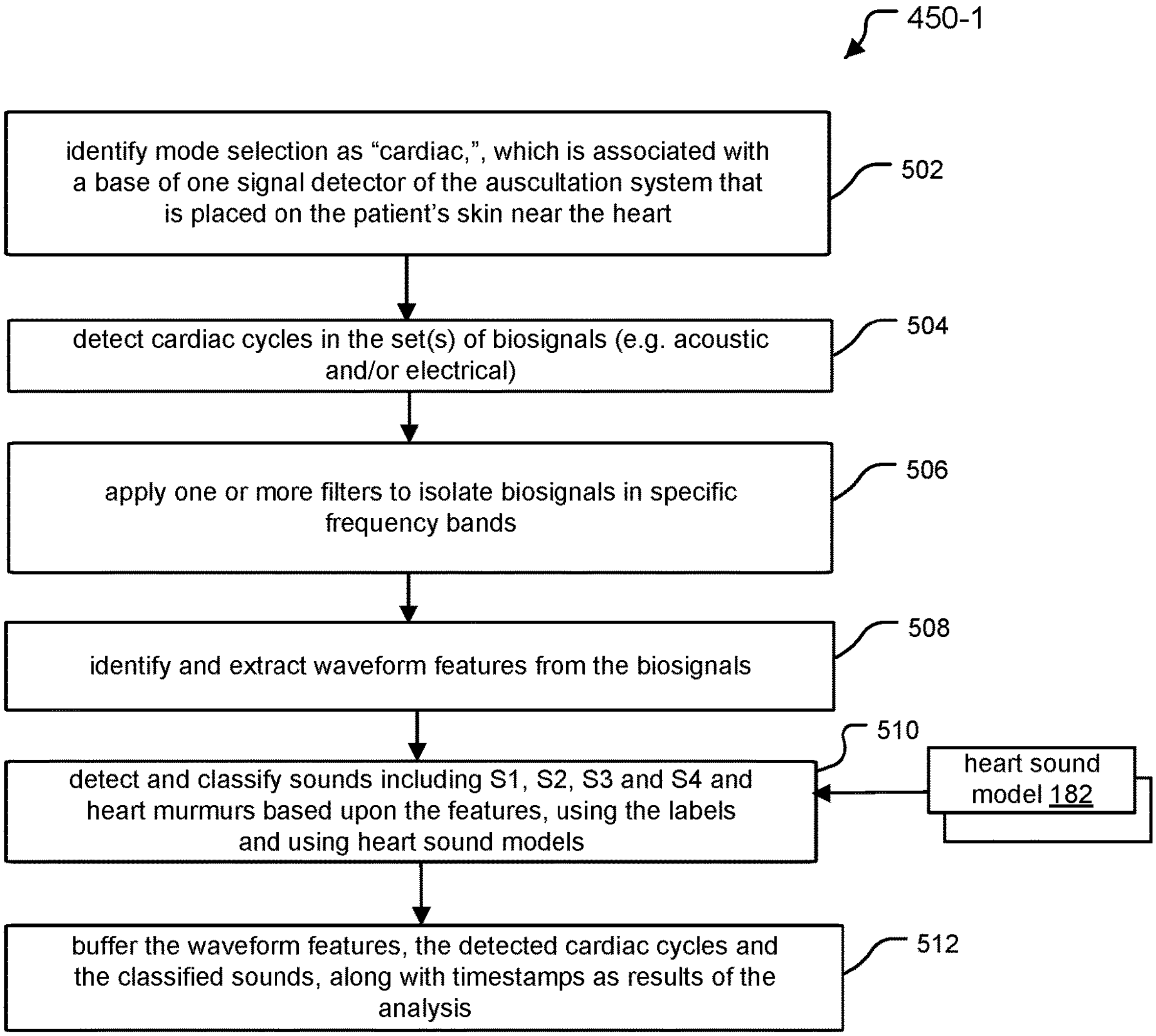
FIG. 6 is a flowchart that provides more detail for the method of FIG. 5, where the flowchart describes operation of the data analysis system when the auscultation system is configured in cardiac mode.

FIG. 6 is a flowchart that provides more detail for the method of FIG. 5. Specifically, the flowchart of FIG. 6 provides more detail for step 450 in FIG. 5. This flowchart is indicated by reference 450-1 and describes operation of the data analysis system 109 when the auscultation system 10 is configured to operate in cardiac mode. In the following steps, the term "the method" refers to an action or operation performed by the data analysis system 109.

At step 502, the method identifies the mode as "cardiac," in which the base 230 of typically one signal detector 120 of the detection system 100 is placed on the patient's skin near the heart. According to step 504, the method detects cardiac cycles in the set(s) of biosignals 101 (e.g. acoustic and/or electrical biosignals). In step 506, the method applies one or more filters to isolate biosignals 101 in specific frequency bands, and in step 508 identifies and extracts waveform features from the biosignals 101.

In step 510, the method detects and classifies sounds including normal sounds S1 and S2, abnormal sounds S3 and S4 and also heart murmurs based upon the features, using the labels and using the heart sound models 182. Then, in step 512, the method buffers the waveform features, the detected cardiac cycles and the classified sounds, along with timestamps as results of the analysis. Upon completion of step 512, control then returns to the end of step 450 in the method of FIG. 5.

When the auscultation system 10 is configured and operating in cardiac mode and the patient is engaged in an interactive session with the system 10, the data analysis system 109 (and/or a medical professional 110 participating in the session with the patient 30) can instruct the patient to perform various actions. These instructions might include directing the patient 30 to move the signal detector 120 to different locations of or near the heart at different times, such as placing the signal detector 120 near the aorta or chambers of the heart, in examples.

In another example, when the medical professional 110 is the patient's primary care physician or practitioner, the medical professional might instruct the patient 30 to take various prescription heart medications (e.g., nitroglycerin) in response to the results of the analysis, and then instruct the patient 30 to repeat steps/tests of the cardiac mode to gauge effectiveness of the medications/treatment. Additionally and/or alternatively, the medical professional 110 might instruct the patient 30 to sit still or possibly engage in specific physical activity for a time period and then repeat steps/tests of the cardiac mode.

Figure 7A:
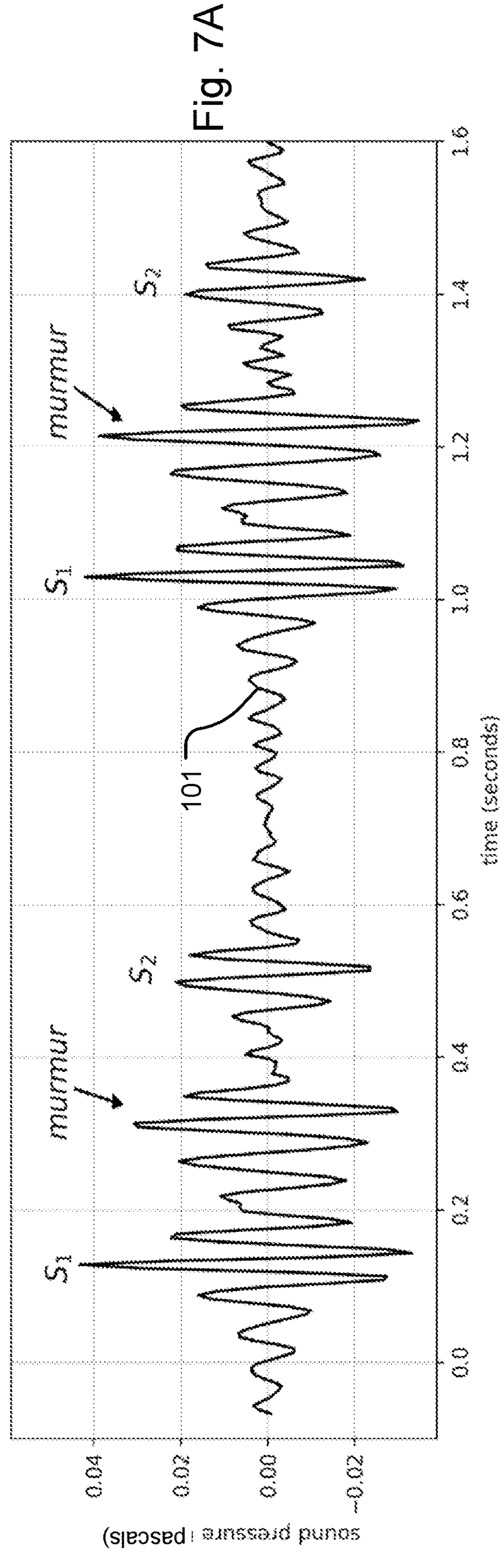
FIG. 7A-7D are exemplary plots of heart sounds of a patient over two heart cycles, based upon biosignals from the body of the patient detected by and sent from the detection system when the auscultation system is configured to operate in cardiac mode, where.
Figure 7B:
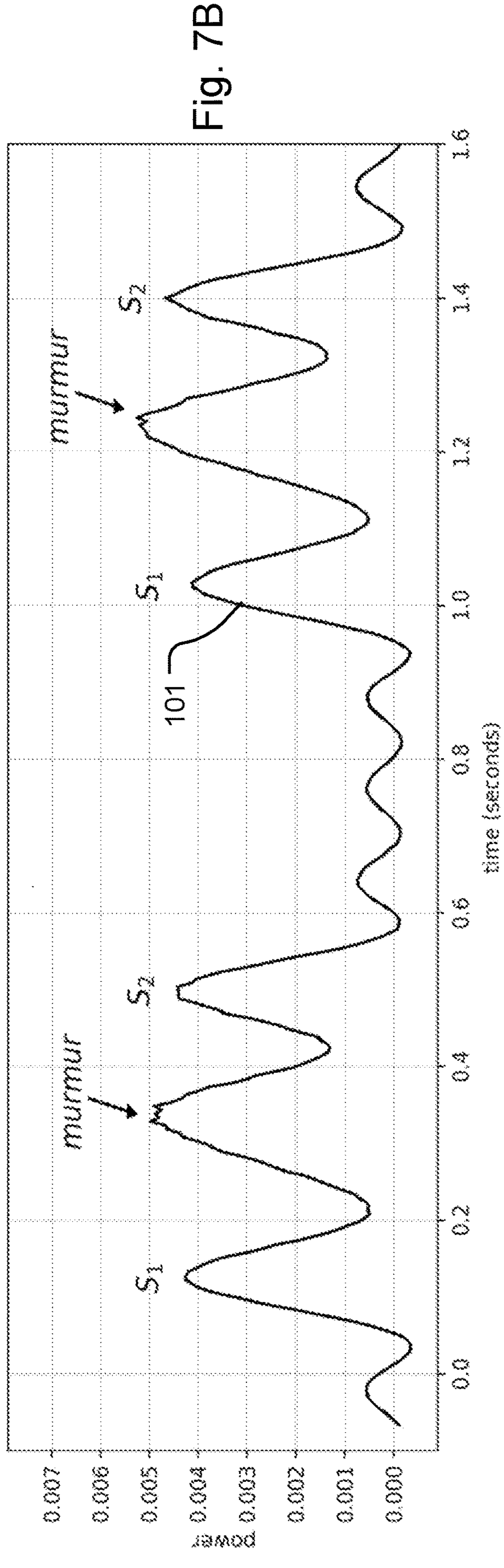
Figure 7C:
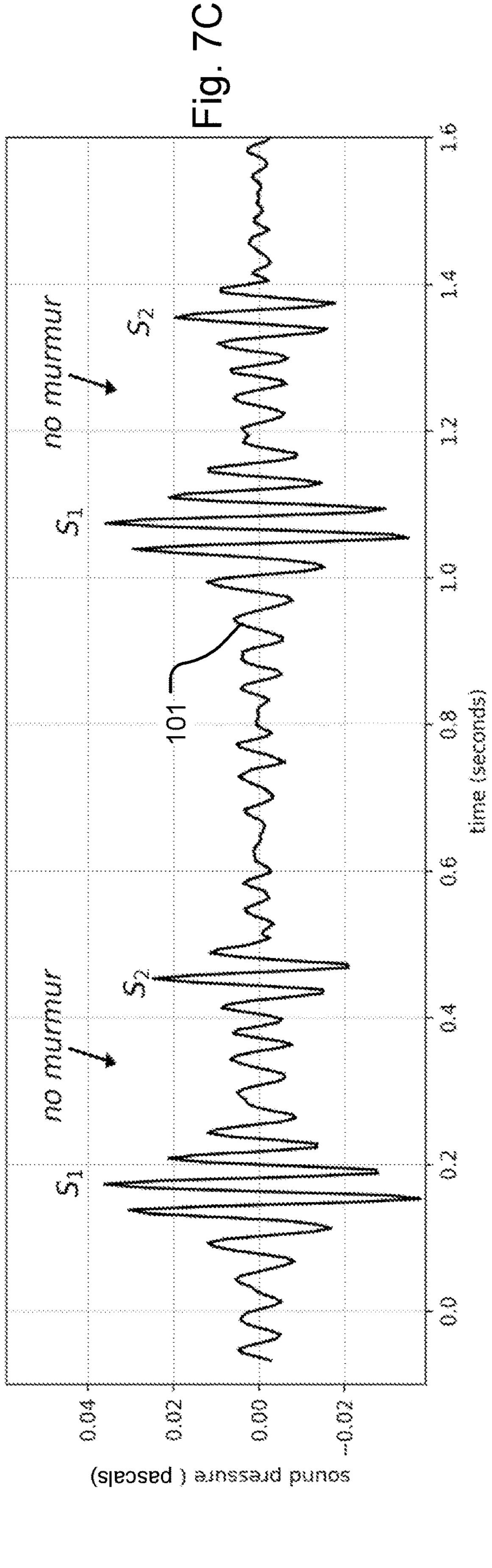
Figure 7D:
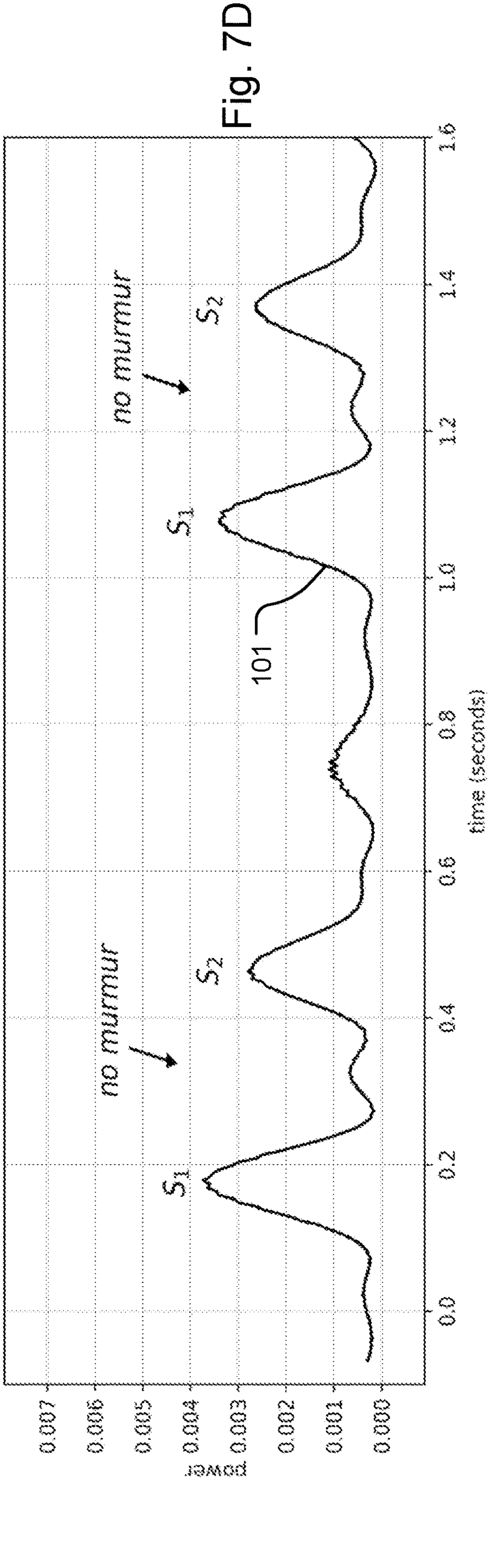

FIG. 7A-7D are plots associated with operation of the auscultation system 10 when configured to operate in cardiac mode. FIGS. 7A and 7B show heart sounds of a patient detected by and sent from a detection system 100 such as in FIG. 1, when the patient 30 is experiencing cardiac murmurs. In contrast, FIGS. 7C and 7D show heart sounds of the patient detected by and sent from the detection system 100 when no murmurs are present. Each of the plots are shown over a period of 1.6 seconds, over which approximately two cardiac cycles occur.

In more detail, FIG. 7A shows heart sounds that the data analysis system 109 has generated based upon biosignals 101 from the body of a patient 30. The biosignals 101 were detected by and sent from a detection system 100 such as in FIG. 1, where the signal detector 120 is instead placed at the patient's heart. Normal heart sounds S1 and S2 for the patient 30 are shown over a period of approximately 1.6 seconds/over approximately two heart cycles. Abnormal sounds S3 and S4 were not exhibited by the patient 30 and are not shown.

Murmurs are also shown in FIG. 7A and indicated as such in the figure. The murmurs are identified as an erratic sound signal between the S1 and S2 sounds. In the example, the patient 30 was previously diagnosed with systolic heart murmurs.

FIG. 7B is a power spectrum plot of the heart sounds in FIG. 7A. In the plot, peaks in the power at S1 and S2 are shown. The power nearly vanishes between S2 and S1, where little cardiac sound is emitted. However, between S1 and S2, where there are significant heart murmurs, a peak corresponding to the heart murmur is seen.

The normal heart sounds S1 and S2, as well as the abnormal sounds S3 and S4, can be identified by a simple peak finding algorithm. For example, with reference to FIG. 7B, the power emitted in some frequency band can be computed, and the peaks coming from S1, S2, S3, and S4 can then be defined as those which exist beyond some threshold. The determination of the heart sounds S1, S2, S3, and S4 can also be aided by machine learning models/algorithms 186.

The heart murmurs can be detected by identifying excess sounds between S1 and S2, and between S3 and S4 (if sounds S3 and S4 exist). This can be accomplished, in one example, by searching for excess power emitted between the heart sounds S1, S2, S3 and S4. Murmur detection can also be aided by machine learning models/algorithms 186.

In a similar vein, FIG. 7C shows heart sounds that the data analysis system 109 has generated based upon biosignals 101 from the body of the same patient. In contrast to the plot of FIG. 7A, no murmurs are present in FIG. 7C.

FIG. 7D shows a power spectrum plot of the heart sounds in FIG. 7C. In the plot of FIG. 7D, peaks in the power at S1 and S2 are shown. The power nearly vanishes between S2 and S1, where little cardiac sound is emitted. The signal is effectively flat between the S1 and S2 peaks, indicating no murmurs.

Figure 8:
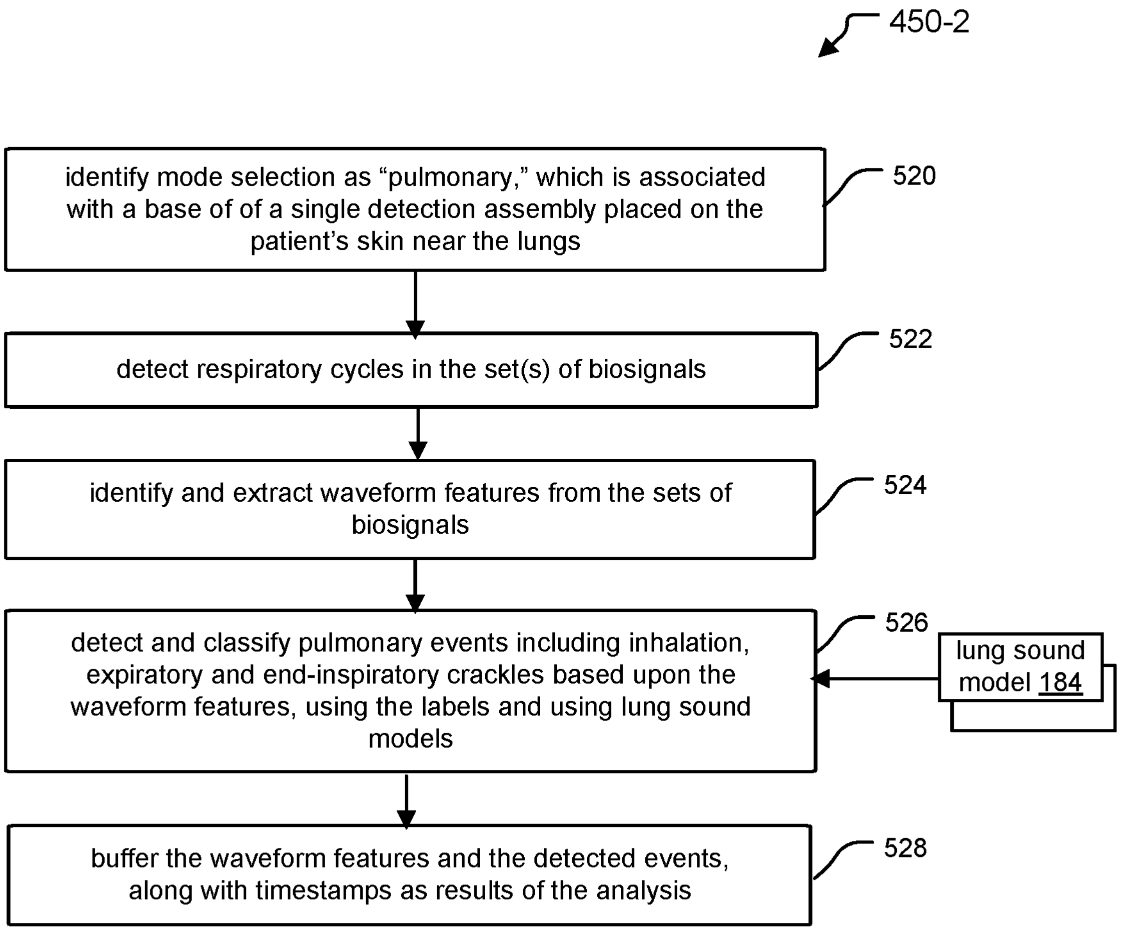
FIG. 8 is a flowchart that provides more detail for the method of FIG. 5, where the flowchart describes operation of the data analysis system when the auscultation system is configured in pulmonary mode.

FIG. 8 is a flowchart that also provides more detail for the method of FIG. 5. Specifically, the flowchart of FIG. 8 provides more detail for step 450 in FIG. 5 and is indicated by reference 450-2. The flowchart describes operation of the data analysis system 109 when the auscultation system 10 is configured to operate in pulmonary mode. In the following steps, the term "the method" refers to an action or operation performed by the data analysis system 109.

Auscultation of the lungs is an effective tool to diagnose lung disorders. Lung sounds, caused by airflow during inspiration or expiration, can be observed over nearly all parts of the chest. The lung sounds can be continuous or short in duration compared to the respiratory period.

One particular abnormal lung sound, crackles (also known as rales) is named for the crackling sounds that a patient's lungs exhibit when fluid is present in the lungs. This fluid can be caused due to medical conditions including bronchitis, asthma, pneumonia and pulmonary edema, in examples. When a patient with fluid in their lungs breathes air during inspiration, small airways of the lungs can be partially or completely blocked with fluid, which can be heard as typically high frequency sounds in the 200 Hz-2000 Hz range.

Pulmonary edema is an elementary feature of congestive heart failure. Aside from end-inspiratory crackles, symptoms of pulmonary edema detectable with auscultation can also include the presence of the third heart sound S3. The method begins at step 520.

At step 520, the method identifies the mode of the auscultation system 10 as "pulmonary," in which the base 230 of typically one signal detector 120 of a detection system 100 is placed on the patient's skin in various locations near the lungs. These locations can include the chest, back and side of the patient 30 near the lungs. According to step 522, the method detects respiratory cycles in the set(s) of biosignals 101. In step 524, the method identifies and extracts waveform features from the set(s) of biosignals 101.

In step 526, the method detects and classifies pulmonary events including inhalation, expiratory and end-inspiratory crackles based upon the waveform features, using the labels and using the lung sound models 184. Data can be taken at each location for several respiratory cycles. In one example, the data analysis system 109 can identify crackles based on identifying high frequency peaks, e.g., at 200 Hz-2000 Hz in the spectrograms during inspiration. The identification of crackles can also be aided by employing machine learning models/algorithms 186.

Then, in step 528, the method buffers the waveform features and the detected events, along with timestamps as results of the analysis. Upon completion of step 528, control then returns to the end of step 450 in the method of FIG. 5.

When the auscultation system 10 is configured and operating in pulmonary mode and the patient 30 is engaged in an interactive session with the system 10, the data analysis system 109 can instruct the patient 30 to perform various actions. These actions can include moving the signal detector 120 to different locations of or near the lungs of the patient 30 at different times, such as at the top/middle/bottom of the lungs, either on the patient's back or their chest, in examples. These actions can also include asking the patient to exhale/breath deeply or in a normal fashion with each change in placement of one or more signal detectors.

A medical professional 110 participating in the interactive session with the patient 30 can also guide the patient 30 or change how the system operates. When the medical professional 110 is also the patient's primary care physician or practitioner, in one example, the medical professional might instruct the patient 30 to take various prescription medications (e.g., inhaler) that includes a steroid and/or bronchodilator) in response to the results of the analysis performed by the data analysis system, and then instruct the patient 30 to repeat steps/tests of the pulmonary mode thereafter to gauge effectiveness of the medications/treatment. Additionally and/or alternatively, the medical professional 110 might instruct the patient 30 to sit still, engage in breathing exercises, or possibly engage in specific physical activity for a time period and then repeat steps/tests of the pulmonary mode.

FIG. 9 shows another embodiment of the detection system, indicated by reference 200. The detection system 200 includes a signal detector 220 that includes similar components and operates in a substantially fashion as the signal detector 120 in FIG. 4. However, the signal detector 220 also detects ECG signals/electrical biosignals 101.

In more detail, the signal detector 220 additionally includes one or more ECG sensors 308 (shown in phantom) and electrical terminals 304. The ECG sensors 308 are located at the bottom 302 of the base 230, while the electrical terminals 304 extend outward from the vertical member 232. The ECG sensors 308 are wired to the terminals 304 internally within the body 202. A coupled earbud 103 is wired to the controller board 105 as in FIG. 4.

The controller board 105 and the signal detector 220 are arranged as follows. The earbud 103 is wired to channel C1 of the controller board 105 via earbud connection 106. One end of ECG wire 102 is connected to channel C2 of the controller board 105, and the opposite end of the wire 102 is connected to an ECG plug 305. The ECG plug 305 then connects to the terminals 304 of the signal detector 220.

The network interface 211 of the controller board 105 collects and buffers the biosignals 101 received from the earbud 103 and the ECG sensor 308 over the channels C1 and C2, and forwards the biosignals 101 to a remote device such as the application server 132.

FIG. 10 is a bottom view of the signal detector 220 in FIG. 9. In the illustrated example, the bottom 302 of the base 230 faces the reader. The base 230 includes a lip 306, and two ECG sensors 308 are included within the lip 306.

The signal detector 220 can also include a tunable diaphragm 310 at the bottom 302 of the base 230. Here, the cavity 201 formed within the body 202 is bounded by the inside surface of the body 202 and the diaphragm 310. Typically, the various embodiments of the signal detectors do not include tunable diaphragms; rather, the bottom 302 is open.

FIG. 11 is a top view of the signal detector 220 in FIG. 9. This view allows the membrane 312 to be visible in the figure. The membrane 312 enables removable attachment of the earbud tip 205 of an earbud 103 to/from the vertical member 232 while also providing an airtight seal. The membrane 312 is made from a flexible material such as plastic, rubber, polytetrafluoroethylene (PTFE) or silicone that provides the seal while also enabling the removable attachment of the earbud 103.

Figure 12:
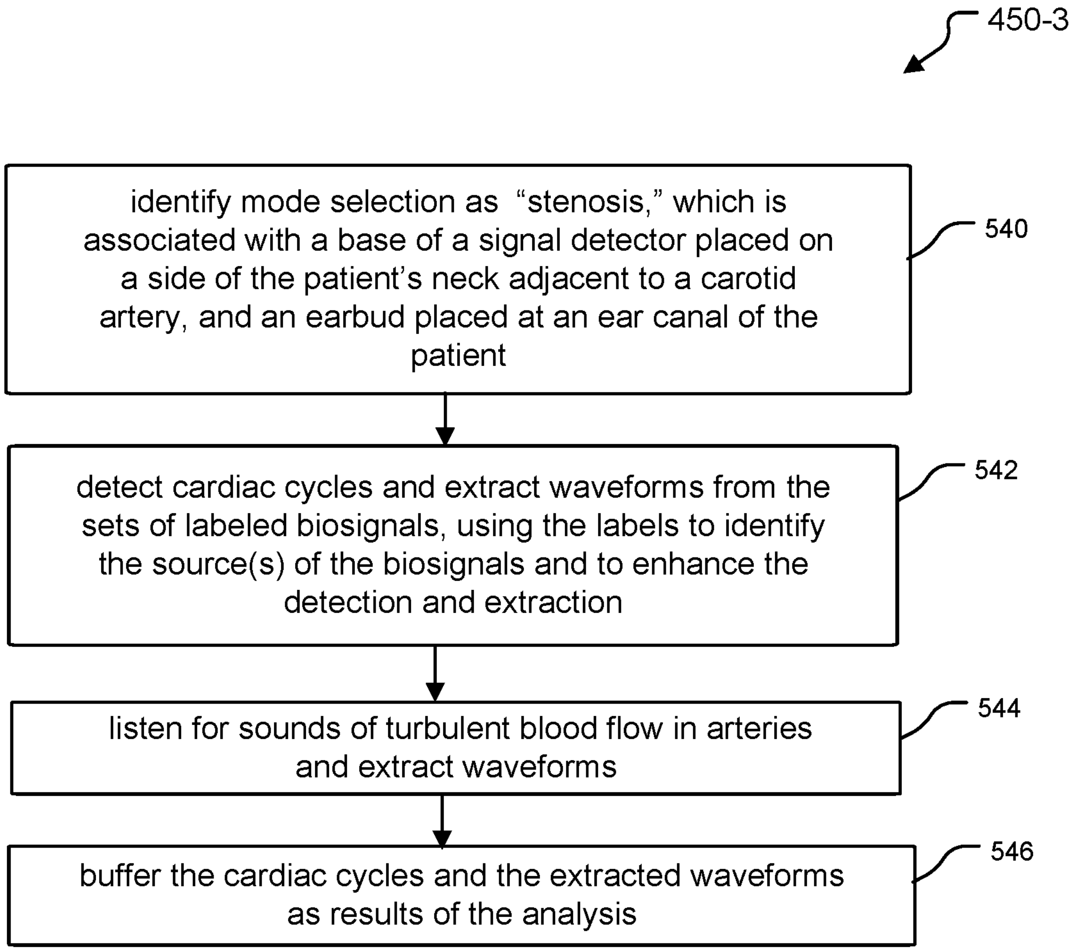
FIG. 12 is a flowchart that provides more detail for the method of FIG. 5, where the flowchart describes operation of the data analysis system when the auscultation system is configured in stenosis mode.

FIG. 12 is a flowchart that provides more detail for the method of FIG. 5. Specifically, the flowchart provides more detail for step 450 in FIG. 5 and is indicated by reference 450-3. The flowchart describes operation of the data analysis system 109 when the auscultation system 10 is configured to operate in stenosis mode. In the following steps, the term “the method” refers to an action or operation performed by the data analysis system 109.

The detection system 100 in FIG. 1 and FIG. 4 is preferably used when the auscultation system 10 is configured to operate in stenosis mode. Here, the method is directed to detection and analysis of carotid artery stenosis, in one example. As shown in FIG. 1, the first earbud 103-1 (which is coupled to the signal detector 120) and the second earbud 103-2 are preferably located on opposite sides of the patient’s head/neck.

The primary purpose of the stenosis module/stenosis mode is to detect aortic stenosis and carotid artery stenosis and/or stenosis of valves within arteries. Carotid artery stenosis is also known as carotid stenosis. Carotid stenosis is the narrowing of the carotid artery due to the accumulation of plaque on interior walls of the arteries. The plaque can break off from the walls and create blood clots. It can also travel to the brain, resulting in stroke. The risk of stroke can thus be gauged by evaluating the presence of carotid stenosis, in conjunction with possibly other factors. However, stenosis of other arteries Indicia of carotid stenosis can be detected via auscultation. The narrowing of the carotid artery can produce turbulence in the blood flow during systole. The turbulent flow can strongly interact with the arterial walls, producing sound that is detectable via auscultation. These turbulent sounds, also known as carotid bruits, are strong clinical predictors of likely carotid artery disease.

Aortic stenosis is the narrowing of the aortic valve. When the aortic valve narrows, abnormal pressure builds up in the left ventricle, and creates a nozzle-like effect when blood is ejected through the aortic valve and into the aorta during systole. The turbulence generated via this nozzle effect then can interact with the aorta, generating sounds that can be heard during auscultation as far away as the neck.

Additionally, pulse waves of a patient with aortic stenosis also have a different waveform than those of healthy individuals. Pulse waves of healthy patients during systole generally have sharp rises in their cardiac signal leading to each peak, and sharp falls after each peak. In contrast, patients with aortic stenosis typically have more gradual rises and falls after each peak during systole. In particular, the buildup of pressure in the left ventricle results in a triangular-shaped waveform due to the fact that the pressure in the left ventricle cannot be released quickly when the aortic valve opens. Rather, the pressure is released slower than in a healthy patient.

Aortic stenosis can be distinguished from carotid artery stenosis as follows. Both produce turbulent sounds which can be heard in the neck during auscultation. Carotid artery stenosis, however, produces more sound above the level of the patient’s clavicle than aortic stenosis or other heart murmurs. However, this increased sound intensity is difficult for even trained medical professionals to distinguish via auscultation using standard stethoscopes. In contrast, the auscultation system 10 can readily detect and distinguish aortic stenosis from carotid artery stenosis. Moreover, the triangular-shaped cardiac waveform during systole associated with aortic stenosis is typically not found with carotid stenosis.

A detection system 100 such as in FIG. 1 is preferably used for the stenosis mode of the auscultation system 10. For example, with reference to FIG. 1, assume the patient 30 has carotid artery stenosis in their right carotid artery As a result, the waveform of the biosignals 101 obtained from the earbud 103-1 of the signal detector 120 during systole should contain fine structure inherent to turbulence (e.g. have a power law spectrum, including audible frequencies). However, the waveform of the biosignals 101 obtained from the earbud 103-2 at the patient’s ear should be dominated by infrasound, with rises and falls correlated with the rapid ejection phase and the left ventricular ejection time. The method begins in step 540.

At step 540, the method identifies the mode as "stenosis," in which the base 230 of the signal detector 120 of the detection system 100 is placed on a side of the patient's neck adjacent to a carotid artery.

According to step 542, the method detects cardiac cycles and extracts waveforms from the set(s) of labeled biosignals 101, using the labels to identify the source(s) of the biosignals 101 and to enhance the detection and extraction. In step 544, the method listens for or otherwise identifies sounds of turbulent blood flow in arteries. The turbulent sounds are usually associated with narrowing and/or a partial blockage of the arteries and are characterized by a "whoosh" sound that the detection system 100 detects. The narrowing is typically caused by plaque that builds up on walls of the arteries over time. Plaque includes fat, cholesterol, and possibly other substances.

Then, in step 546, the method buffers the cardiac cycles and the extracted waveforms as results of the analysis. Upon conclusion of step 546, control passes to the end of step 450 in FIG. 5.

When the auscultation system 10 is configured and operating in stenosis mode and the patient 30 is engaged in an interactive session with the system 10, the data analysis system 109 can instruct the patient 30 to perform various actions. These might include moving the signal detector 120 to different locations of the neck adjacent to either the left carotid artery, the right carotid artery or both, and placing the second earbud 103-2 at either the left or right ear canal.

It can also be appreciated that the method of FIG. 12 can be used to detect stenosis in arteries other than the carotid arteries. In one example, stenosis of the aorta and/or stenosis of its valves can be determined. In another example, the method might be applied to renal arteries. Here, the base 230 of the signal detector 120 would be placed on the skin near a renal artery of a kidney on one side of the patient's body, and the second earbud would be placed at the ear canal on the opposite side of the patient's body.

FIG. 13A through 13D are signal plots that collectively form a Wiggers Diagram. The plots show cardiac activity of a patient diagnosed with aortic stenosis over three cardiac cycles. FIG. 13A through FIG. 13D respectively show an echocardiogram, a plot of cardiac signals obtained by cardiac catheterisation, a plot of cardiac biosignals 101 obtained by the auscultation infrasound system 10, and an ECG.

Figure 13A:
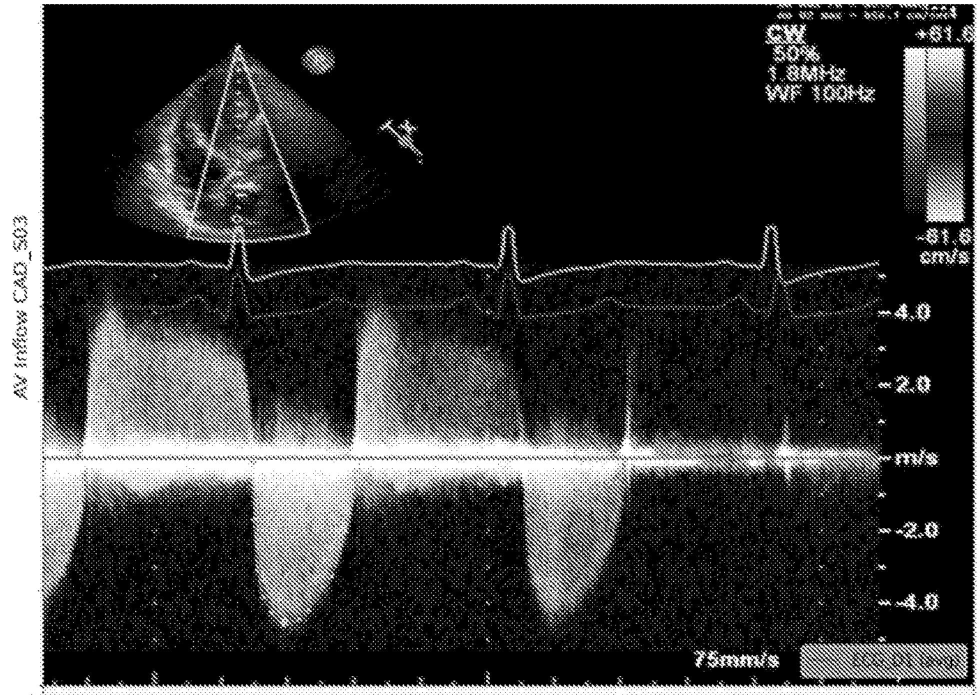
FIG. 13A through 13D are signal plots that collectively form a Wiggers Diagram, where the plots show cardiac activity of a patient with aortic valve stenosis, and where.
Figure 13B:
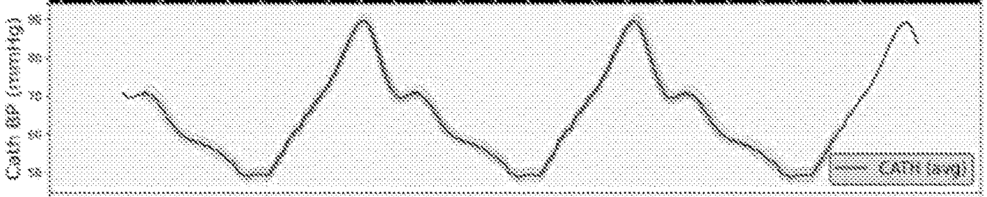
Figure 13C:
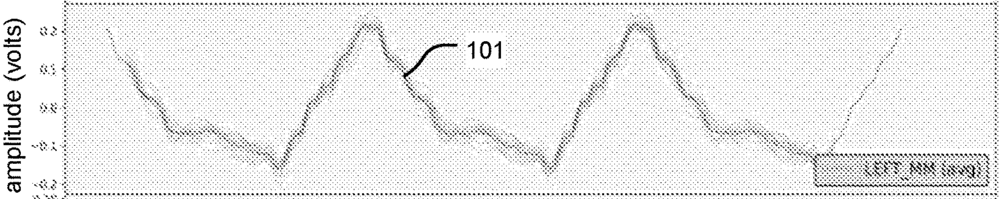
Figure 13D:
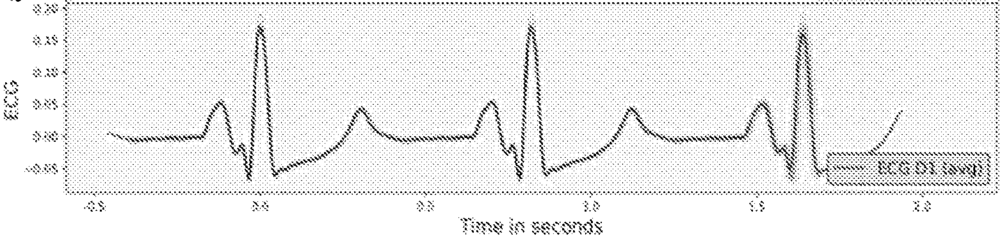

In FIG. 13C, the biosignals 101 were detected by and sent from earbud 103-2 placed in the patient's ear. The triangular-shaped waveform of the biosignals 101 is associated with the decreased pressure in the aorta due to the aortic stenosis, as compared to healthy individuals.

Figure 14:
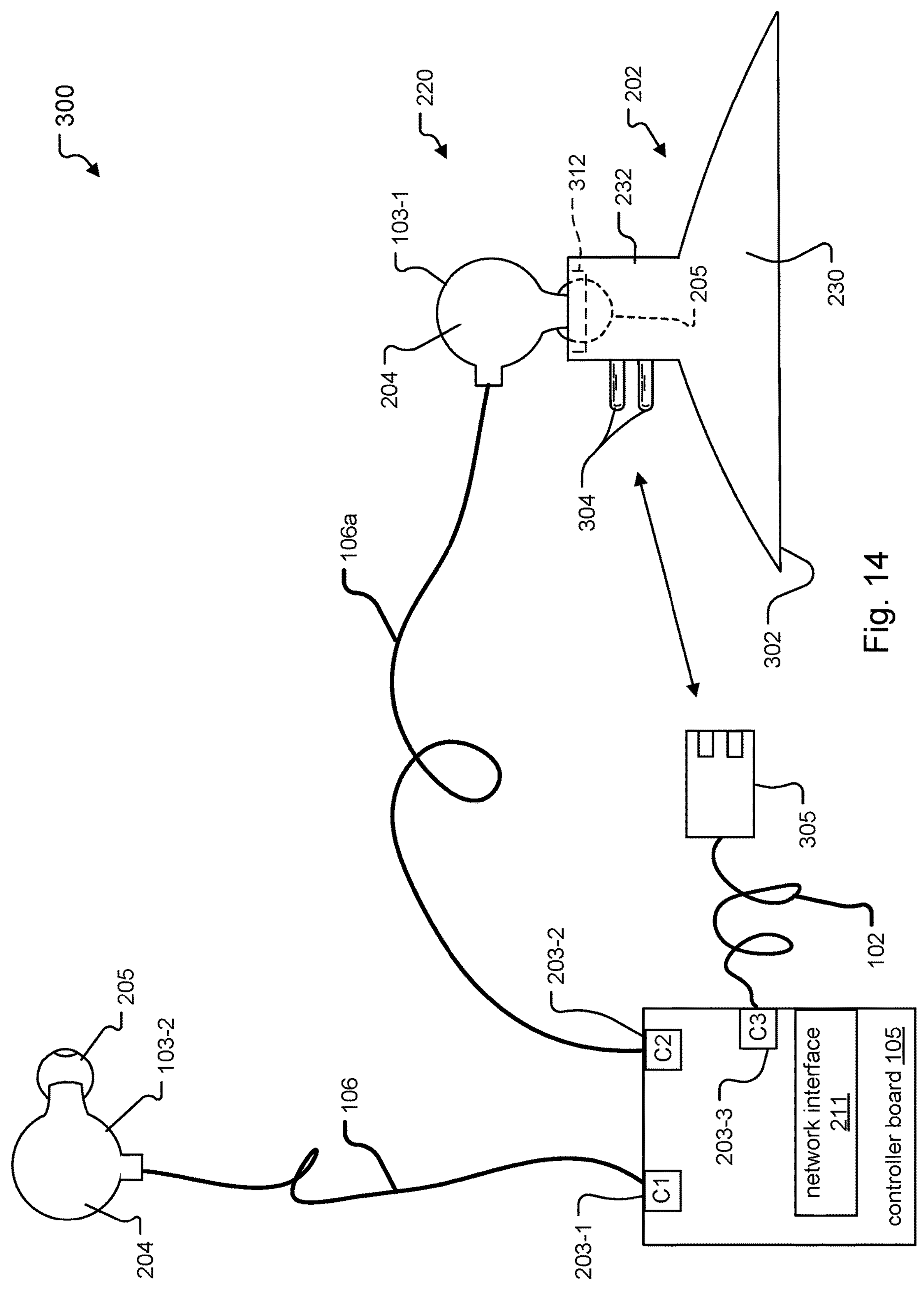
FIG. 14 is a schematic diagram that shows another embodiment of the detection system of the auscultation system, where the detection system includes a signal detector as in FIG. 9 and includes a second earbud for placement at the ear canal of the patient as shown in FIG. 4.

FIG. 14 shows another embodiment of the detection system, indicated by reference 300. The detection system 300 includes an ECG-equipped signal detector 220 as in FIG. 9, and includes a second earbud 103-2 for placement at the ear canal of the patient 30 as in FIG. 4.

The controller board 105 includes channels 203-1 through 203-3, also labeled as C1, C2 and C3, respectively, and the network interface 211. The second earbud 103-2 is wired to channel C1 via earbud connection 106, the first earbud 103-1 is wired to channel C2 via a different earbud connection 106*a*, and the ECG terminals 304 connect to channel C3 via ECG wire 102 and its ECG plug 305.

Figure 15:
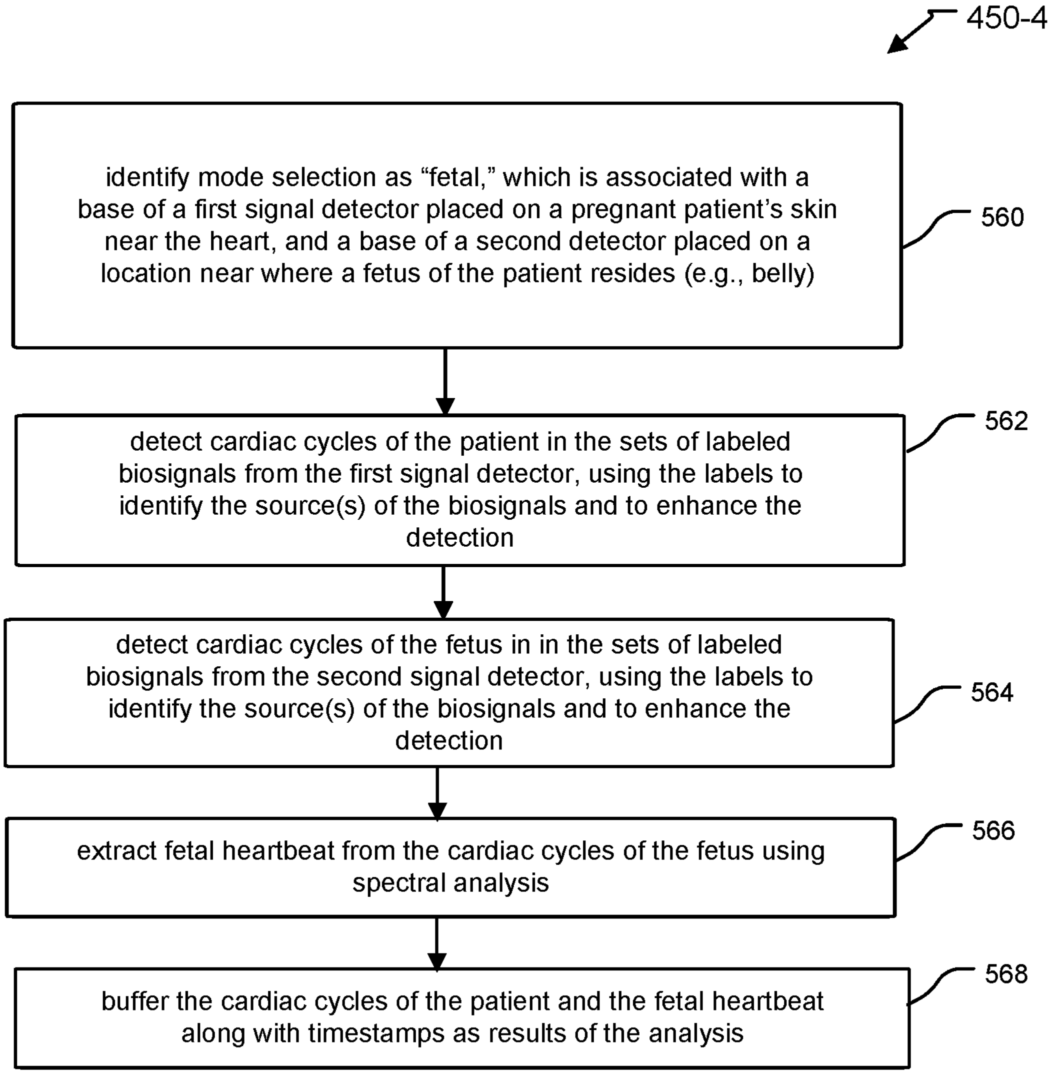
FIG. 15 is a flowchart that provides more detail for the method of FIG. 5, where the flowchart describes operation of the data analysis system when the auscultation system is configured in fetal heartbeat mode.

FIG. 15 is a flowchart that provides more detail for the method of FIG. 5. Specifically, the flowchart provides more detail for step 450 in FIG. 5 and is indicated by reference 450-4. The flowchart describes operation of the data analysis system 109 when the auscultation system 10 is configured to operate in fetal heartbeat mode ("fetal"). In the following steps, the term "the method" refers to an action or operation performed by the data analysis system 109. The method begins at step 560.

At step 560, the method identifies the mode as "fetal," in which the base 230 of a first signal detector 120 of the detection system 100 is placed on a pregnant patient's skin near the heart, and the base 230 of a second signal detector 120 is placed on a location near where a fetus of the patient resides (e.g., belly of patient 30).

According to step 562, the method detects cardiac cycles of the patient 30 in the sets of labeled biosignals from the first signal detector 120, using the labels to identify the source(s) of the biosignals 101 and to enhance the detection. In step 564, the method detects cardiac cycles of the fetus in the sets of labeled biosignals 101 from the second signal detector 120, using the labels to identify the source(s) of the biosignals and to enhance the detection. Typically, the biosignals 101 are obtained for a set of continuous cardiac cycles over a period of 30 to 60 seconds.

In step 566, the method extracts a fetal heartbeat from the cardiac cycles of the fetus using frequency domain analysis such as spectral analysis. Then, in step 568, the method buffers the cardiac cycles of the patient and the fetal heartbeat, along with timestamps as results of the analysis. Upon conclusion of step 568, control passes back to the end of step 450 in FIG. 5.

In examples, the mother's cardiac cycle can be observed from the presence of S1 and S2 heart sounds, in accordance with the cardiac mode of FIG. 6 and its associated processing by the data analysis system 109. For this purpose, in one example, a spectral analysis of the biosignals 101 from the mother's chest can be used to identify the mother's heart rate. Alternatively, the mother's heart rate can be determined based on the spacing between adjacent S1 heart sounds. Likewise, a spectral analysis of the biosignals 101 from the mother's belly can be used to identify the fetal heart rate, which should in general be significantly higher than that of the mother.

When the auscultation system 10 is configured and operating in fetal mode and the patient 30 is engaged in an interactive session with the system 10, the data analysis system 109 (and/or a medical professional 110 participating in the session with the patient 30) can instruct the patient to perform various actions. These might include moving the signal detectors 120 to different locations of the patient near her heart or belly, in examples.

Figure 16:
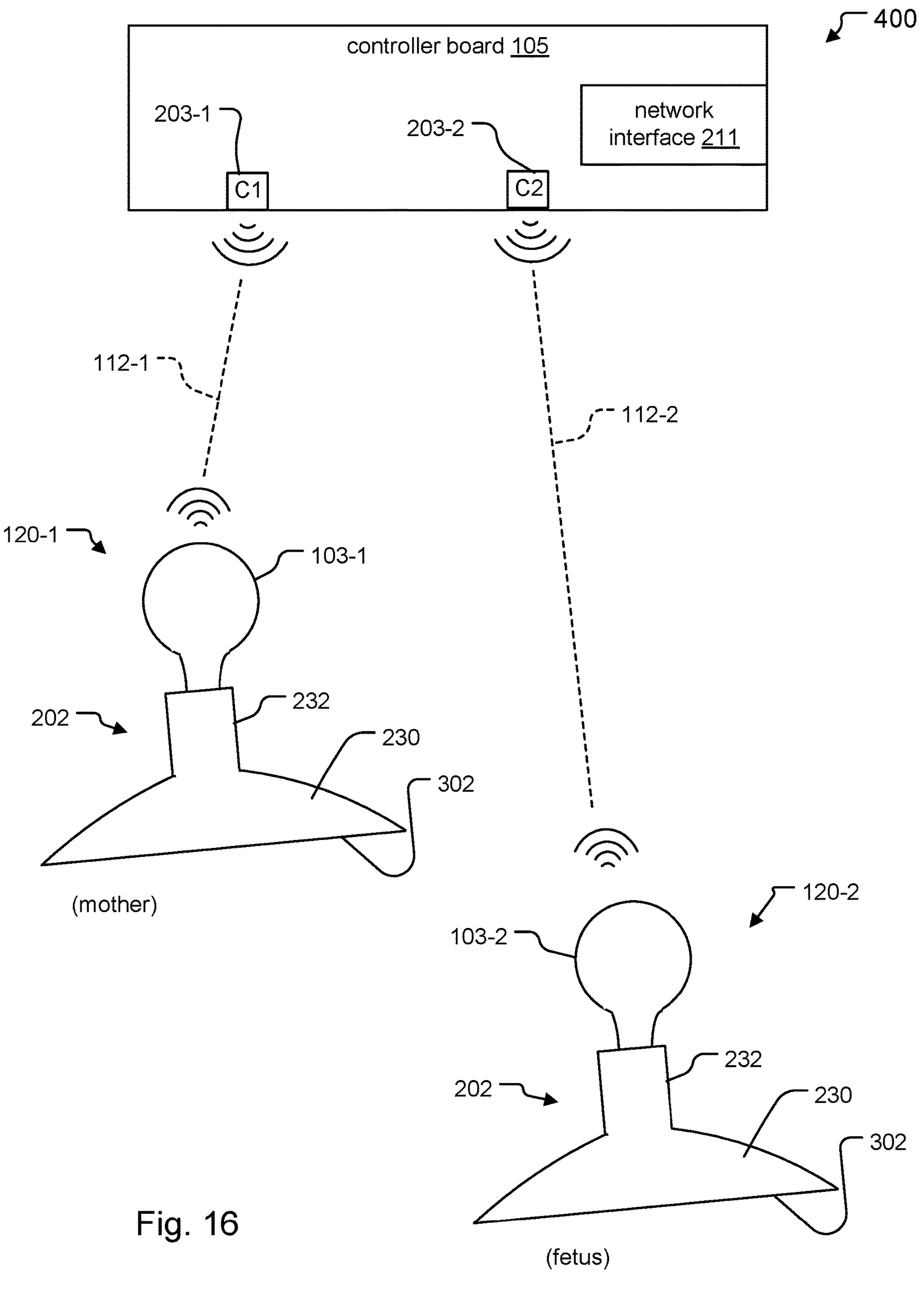
FIG. 16 is a schematic diagram that shows yet another embodiment of the detection system of the auscultation system, where the detection system includes two signal detectors constructed as in FIG. 4 but are instead wirelessly connected to the controller board, and where the auscultation system is configured in fetal heartbeat mode.

FIG. 16 shows yet another embodiment of the detection system, indicated by reference 400. The detection system 400 includes two signal detectors 120-1 and 120-2 that include similar components and operate in a substantially fashion as the signal detector 120 in FIG. 4. However, the signal detectors 120-1, 120-2 each support wireless communications.

The first signal detector 120-1 includes a first earbud 103-1, and is intended for placement at/near the heart of a pregnant patient 30. The second signal detector 120-1 includes a second earbud 103-2, and is intended for placement at/near the belly of the pregnant patient 30 where the fetus resides. The controller board 105 includes channels 203-1 and 203-2, also labeled as C1 and C2, respectively and the network interface 211. First earbud 103-1 establishes a wireless link 112-1 with channel C1 and second earbud 103-2 establishes a wireless link 112-2 with channel C2.

In another embodiment, the controller board 105 is removed, and the earbuds 103-1, 103-2 of the first and second signal detectors 120-1 and 120-2 directly forward the detected biosignals via network interfaces 176 of the earbuds. The network interfaces of the earbuds/signal detectors then forward the biosignals 101 to the API 134 of the application server 132.

Figure 17:
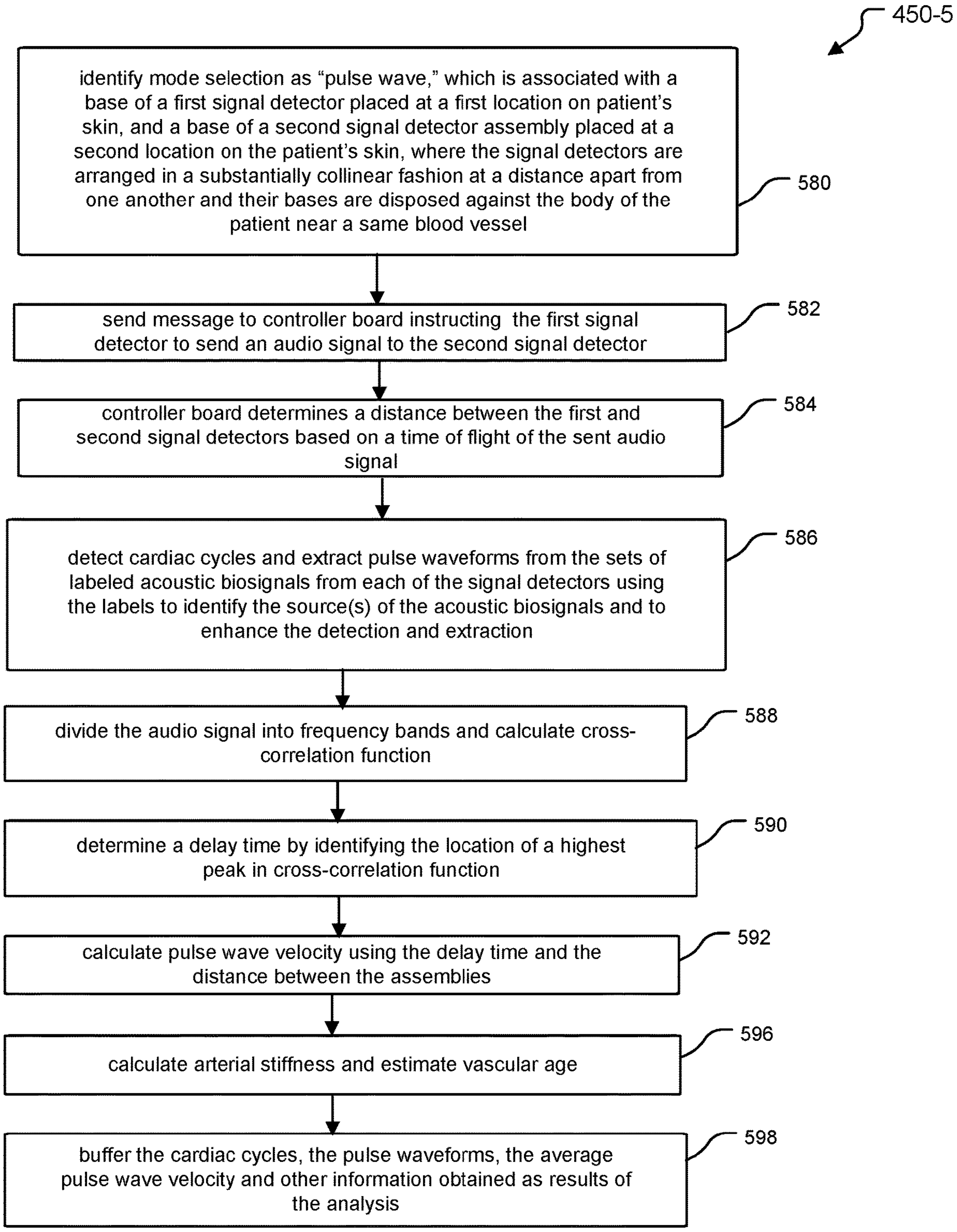
FIG. 17 is a flowchart that provides more detail for the method of FIG. 5, where the flowchart describes operation of the data analysis system when the auscultation system is configured in pulse wave mode.

FIG. 17 is a flowchart that provides more detail for the method of FIG. 5. Specifically, the flowchart provides more detail for step 450 in FIG. 5 and is indicated by reference 450-5. The flowchart describes operation of the data analysis system 109 when the auscultation system 10 is configured to operate in pulse wave mode. In the following steps, the term "the method" refers to an action or operation performed by the data analysis system 109.

By way of background, during each cardiac cycle, pulse waves are generated which propagate from the heart downstream along the arteries. The pulse waves propagate at a speed ranging from 5-30 m/s, which is much slower than the speed of sound in tissue (which is on the order of 1500 m/s). According to the Moens-Korteweg equation, the pulse wave velocity is proportional to the square root of the elastic modulus of the blood vessel. Hence the pulse wave velocity is a probe of arterial stiffness. This is important because arterial stiffness is a valuable measure of cardiovascular health and a predictor of hypertension.

The pulse wave velocity can be measured by detecting the time lag between a pulse wave arriving at two different locations along an artery. However, measurements of the pulse wave velocity can be complicated by the fact that pulse waves can scatter off arterial junctions. This can result in a distortion of the pulse waveform as it propagates farther downstream, past more and more junctions. Because of this side effect, it is preferable to measure the pulse wave velocity along a segment of an artery without any branches.

At the same time, restricting the measurement to arterial segments without branches has tradeoffs. In one example, the distance between two measurement points must be smaller than a measurement from the carotid to femoral arteries, in one example. As a result, the measurement devices must be sensitive to short time scales. For example, a pulse wave propagating over a distance z=25 cm at speed v=10 m/s will only result in a lag time of z/v=0.025 seconds.

The auscultation system 10 can measure the pulse wave velocity because pulse waves themselves create a disturbance which propagates through tissue, thereby producing low frequency vibrations on the surface of the skin. These pulse waves can be detected along the radial artery in the patient's forearm or elsewhere in the body. The method begins at step 580.

In step 580, the method identifies the module type as "pulse wave," in which the base 230 of a first signal detector 120-1 is placed at a first location on the patient's skin, and the base 230 of a second signal detector 120-2 is placed at a second location on the patient's skin. The signal detectors 120 are arranged in a substantially collinear fashion at a distance apart from one another and their bases 230 are disposed against the body of the patient 30 near the same blood vessel.

At this point, a distance between the earbuds 103 of the signal detectors 120 is determined. In one example, according to step 582, the method sends a message to the controller board 105 instructing the first signal detector 120-1 to send an audio signal to the second signal detector 120-2. The earbud 103 at the second signal detector 120-2 detects an acoustic pressure associated with the sent audio signal and sends an electrical representation of the detected pressure to the data analysis system 109. The data analysis system 109 correlates (the electronic representation of) the acoustic pressure detected by and sent from each earbud 103.

At step 584, the controller board 105 determines a distance between the first and second signal detectors 120-1, 120-2 based on a time of flight of the sent audio signal. Alternatively, the patient 30 or a medical professional with the patient might physically measure the distance between the earbuds 103 with a ruler. The data analysis system 109 could also determine this distance.

Once the distance between the earbuds 103 is determined, the linear distance along the artery can be inferred using knowledge of basic anatomy (and perhaps using additional information, such as the radius of the arm, in one example). After the distance along the artery is obtained, the method continues in step 586.

In step 586, the method detects cardiac cycles and extracts pulse waveforms from the set(s) of labeled acoustic biosignals 101 from each of the signal detectors, using the labels to identify the source(s) of the acoustic biosignals and to enhance the detection and extraction. In step 588, the method divides the audio signal into frequency bands and calculates a cross-correlation function. In step 590, the method determines a delay time by identifying the location of a highest peak in the cross-correlation function. The method then calculates the pulse wave velocity using the delay time and the distance between the signal detectors 120-1, 120-2 in step 592. For this purpose, the pulse wave velocity is calculated as the distance divided by the delay time.

In step 596, the method calculates an arterial stiffness and estimates vascular age of the blood vessel under test. In step 598, the method buffers the cardiac cycles, the pulse waveforms, the average pulse wave velocity and other information obtained as results of the analysis. Upon conclusion of step 598, control passes back to the end of step 450 in FIG. 5.

Figure 18:
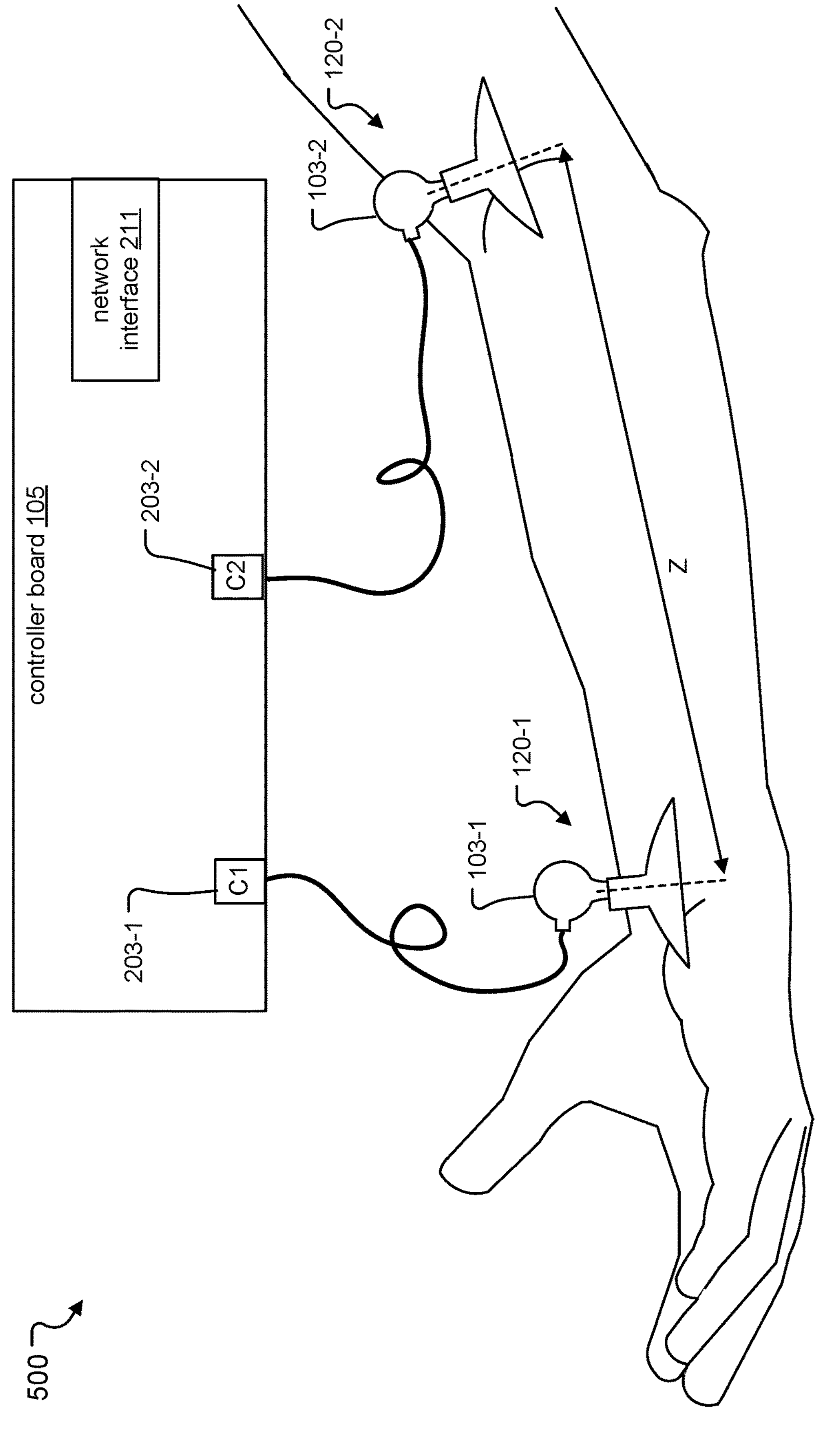
FIG. 18 is a schematic diagram that shows yet another embodiment of the detection system of the auscultation system, where the detection system includes two signal detectors that are each constructed as in FIG. 4, and where the signal detectors are shown placed against an arm of a patient when the system is configured to operate in pulse wave mode.

FIG. 18 shows yet another embodiment of a detection system 500. The detection system 500 includes two signal detectors 120-1 and 120-2 that are wired to the controller board 105. The signal detectors 120-1, 120-2 are similarly constructed and operate in a similar fashion as the signal detector 120 in FIG. 4.

In the illustrated example, the wired signal detectors 120-1 and 120-2 are placed along an arm of a patient 30 when the system 10 is configured to operate in pulse wave mode. Here, the signal detectors 120-1 and 120-2 are placed along the patient's skin at end points of a radial artery of the patient 30. The earbuds 103 of the signal detectors 120 are separated by a distance Z.

With reference to the figure, the wired signal detectors 120-1 and 120-2 detect pressure waves caused by pulse waves that propagate in the radial artery. The pulse waves cause the skin to vibrate at low frequencies. These vibrations create the pressure waves in the air which the wired signal detectors 120-1 and 120-2 can detect.

In more detail, each wired signal detector 120-1, 120-2 detects a pulse of sound as the pulse wave propagates through the artery. Since the speed of sound in tissue is on the order of 1500 m/s, which is much greater than the pulse wave velocity, each signal detector 120-1, 120-2 can detect a pulse of sound which peaks within a fraction of a millisecond after the pulse wave passes by. The pulse wave velocity can then be inferred from the time lag between the signal detectors 120-1, 120-2 as well as knowledge about their separation, which can be used to infer the total distance along the artery the pulse wave has propagated.

Figure 19:
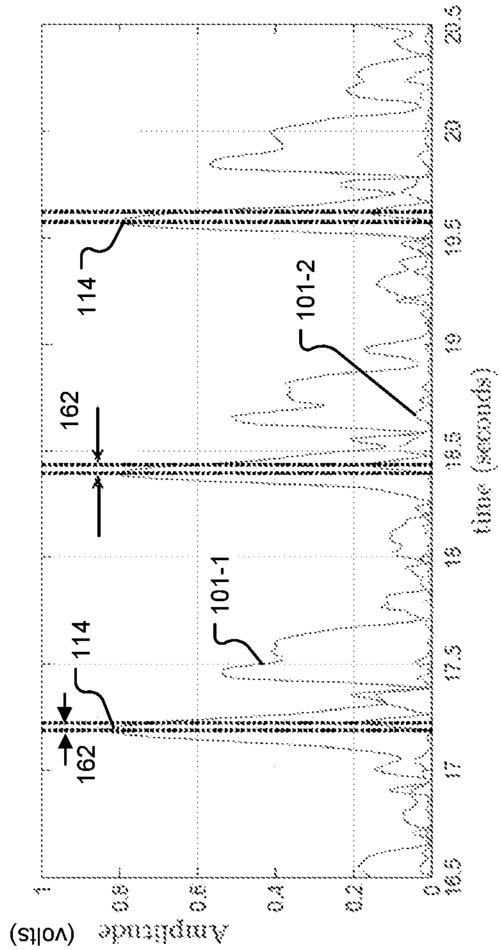
FIG. 19 is a plot of exemplary biosignals obtained from each of the signal detectors in FIG. 18 during pulse wave mode operation of the auscultation system, over a time period of approximately five seconds.

FIG. 19 is a plot of biosignals 101-1 and 101-2 detected by and sent from earbuds 103-1 and 103-2, respectively, in FIG. 18. Peaks 114 in the biosignals 101-1 are shown and correspond to a pulse wave near the earbud 103-1. A time lag 162 between the signal detectors 120-1 and 120-2 is also shown. The biosignals 101-1, 101-2 are plotted over a five second interval.

Figure 20:
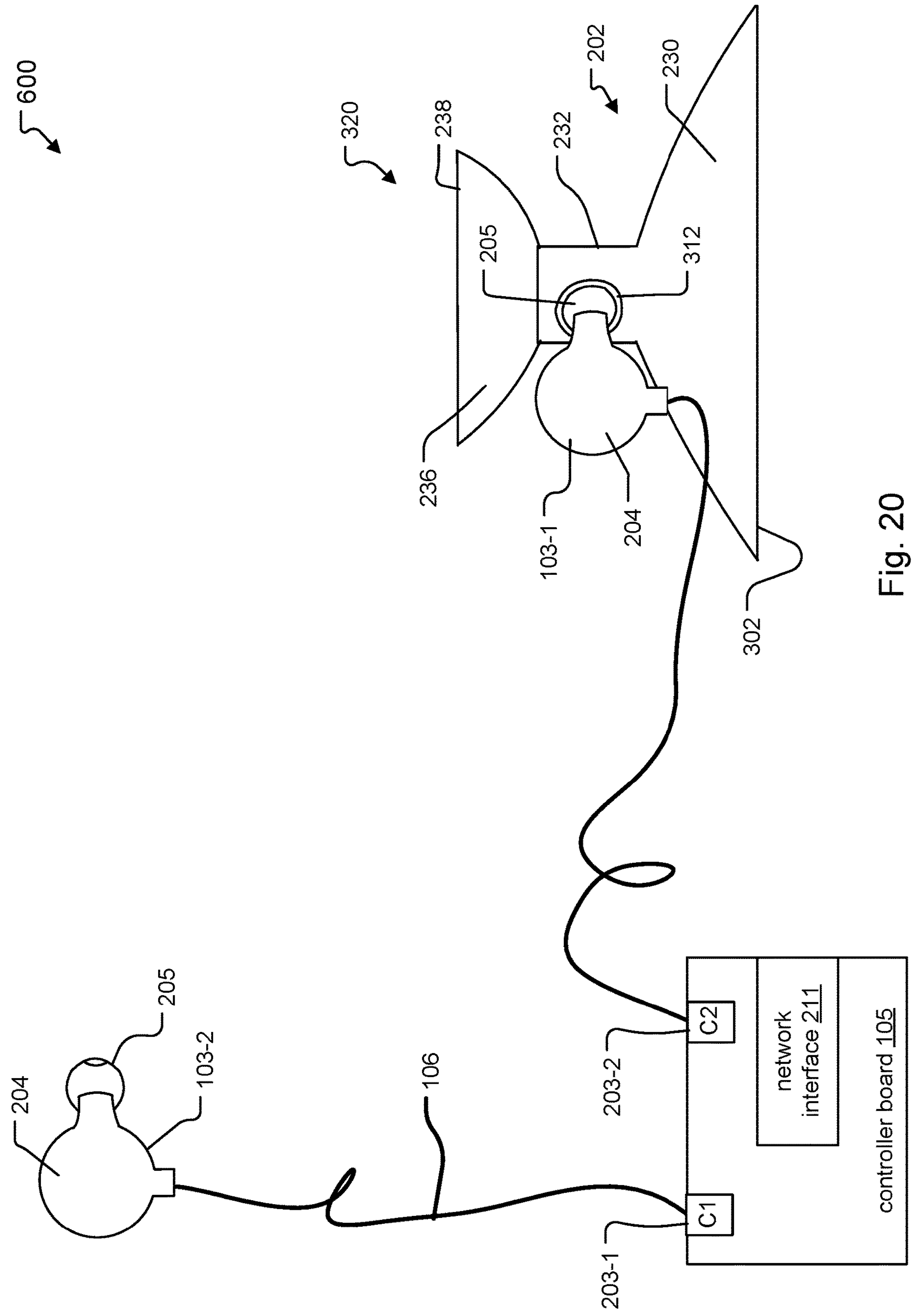
FIG. 20 is a schematic diagram that shows still another embodiment of the detection system of the auscultation system, where the detection system includes a signal detector with a coupled earbud wired to the controller board and includes a second wired earbud placed against the ear canal of the patient as in FIG. 4, and where the signal detector also includes a horn.

FIG. 20 shows still another embodiment of the detection system, indicated by reference 600. The detection system 600 includes another embodiment of a signal detector, indicated by reference 320, and a second wired earbud 103-2 for placement against an ear canal of the patient 30.

The signal detector 320 includes a first earbud 103-1 and a horn 236 attached to the vertical member 232. The membrane 312 is instead incorporated into a side of the vertical member 232 and accepts the earbud tip 205 of the first earbud 103-1.

The horn 236 has a top 238 and is similar in shape to the base 230. However, the horn 236 is intentionally smaller than the base 230. In one implementation, the horn 236 can be removably attached from the vertical member 232 using a press fit, screws, clips, or other attachment mechanism. This enables horns 236 of different sizes and surface areas to be used.

During operation of the detection system 600, rather than the patient placing the bottom 302 of the base 230 against their skin, the patient 30 might instead place the top 238 of the horn 236 against their skin. The patient 30 might do this because of the smaller surface area that the horn 236 occupies on the patient's body as compared to the bottom 302. In this way, the horn 236 might be selected to narrow the area of the patient's body from which the biosignals 101 are detected. In this way, a common base 230 can be used with different horns 236.

It can also be appreciated that each of the embodiments of the auscultation system 10 can include ECG sensors 308 in their signal detectors 120, 220, 320. For the embodiments that include two signal detectors, either one or both of the signal detectors can include at least one ECG sensor, where each of the ECG sensors detect electrical biosignals from the body of the patient 30.

Other configurations of the auscultation system 10 are also possible. In one example, the system 10 may include a detection system with two signal detectors 120-1/120-2 or 120/220, each of which includes a coupled earbud 103, and the system 10 may additionally include a third earbud 103 worn in one ear canal of the patient 30 and optionally a fourth earbud 103 worn in another ear canal of the patient 30.

Additionally and/or alternatively, the auscultation system 10 can continuously identify or otherwise infer problems either with the system 10 or its usage, and suggest correction. For example, the system 10 can identify potential improper placement or usage of the components of the detection systems 100-600 relative to the body of the patient. For this purpose, the data analysis system 109 can extract the motion artifacts from the biosignals 101 detected by and sent from the one or more earbuds/signal detectors, and analyze the motion artifacts, possibly also in conjunction with the biosignals 101 themselves. Based on this information, the auscultation system 10 can facilitate proper positioning of the signal detectors 120, 220, 320 relative to the body of the patient 30, and promote repeatable results over time, in examples.

By way of example, with reference to the embodiment of the detector system 400 in FIG. 16, the data analysis system 109 might identify a significant amount or amplitude of motion artifacts associated with the biosignals 101 detected by and sent from signal detector 120-1 over a time period. For the same time period, the system 109 might identify a much lower amount or amplitude of motion artifacts associated with the biosignals 101 detected by and sent from signal detector 120-2. Based upon this determination, the data analysis system 109 might conclude that the signal detector 120-1 was moving over the time period, and send a notification message 111 to the app 40. The message might suggest that the patient 30 or other individual keep the signal detector 120-1 stationary upon the body of the patient 30 during subsequent test sessions.

In another example, the auscultation system 10 might infer improper positioning of the earbuds 103 and/or signal detectors 120, 220, 320 of the detection systems 100, 200, 300, 400, 500 and 600. The system 10 might infer this based upon from the biosignals 101 detected by the detection systems, possibly also in conjunction with any motion artifacts extracted from the biosignals 101. With reference to the detection system 400 in FIG. 16, for example, the data analysis system 109 could determine that the amplitude of the biosignals 101 from signal detector 120-2 is significantly lower than an amplitude of the biosignals from signal detector 120-1. Based on this determination, the data analysis system 109 might conclude a problem with signal detector 120-2 and/or its usage. In response, the data analysis system 109 might send a notification message 111 to the app 40, where the message instructs the patient to do one or more of the following: verify that the bottom 302 of the base 230 of signal detector 120-2 is entirely placed against the skin of the patient 30; verify that a couplant (wet or dry) between the bottom 302 and the skin has been uniformly applied; verify that the earbud 103-2 is properly seated within the membrane 312 of the body 230; and replace the signal detector 120-2.

In this way, the analysis of the motion artifacts provided by the data analysis system 109, with or without the analysis of their associated biosignals 101, can provide the following exemplary benefits. First, it can assist new patients 30 and/or other individuals when using the auscultation system 10. Second, it can diagnose problems with usage of the earbuds 103 and/or signal detectors 120, 220, 320 or with placement of these components against the body of the patient 30. Third, it can promote repeatable testing results over time. Fourth, it can identify possible failure of components in the system 10. These benefits are provided for all embodiments of the detector systems 100, 200, 300, 400, 500 and 600 of the auscultation system 10.

While this invention has been particularly shown and described with references to preferred embodiments thereof, it will be understood by those skilled in the art that various changes in form and details may be made therein without departing from the scope of the invention encompassed by the appended claims.

What is claimed is:

1. An auscultation system, the system comprising:

a first signal detector that is configured to detect biosignals including infrasonic and audible signals from a body of a patient, wherein the first signal detector includes:

a body; and a first earbud coupled to the body of the signal detector, wherein the first earbud includes an acoustic sensor that is configured to detect the biosignals from the body of the patient, via the body of the first signal detector;

a network interface configured to forward the biosignals from the first signal detector;

a remote device including an application programming interface (API) configured to receive the biosignals forwarded from the network interface; and a data analysis system configured to access the biosignals at the API;

wherein the body of the first signal detector includes a base configured to be positioned against the body of the patient near a heart of the patient; and wherein the data analysis system is configured to determine a heartbeat and heart sounds of the patient based upon the biosignals in conjunction with heart sound models.

2. The system of claim 1, wherein the body of the first signal detector includes a membrane that is configured to enable the coupling of the first earbud to the body of the first signal detector, to provide an acoustic seal between the first earbud and the body of the first signal detector, and to enable removeable attachment of the first earbud from the body of the first signal detector.

3. The system of claim 1, wherein the first signal detector includes at least one ECG sensor that is configured to detect biosignals including electrical biosignals from the body of the patient, and wherein the network interface is configured to forward the electrical biosignals from the first signal detector.

4. The system of claim 1, wherein the first signal detector includes at least one ultrasound transducer that is configured to transmit ultrasound into and/or detect ultrasound reflected from the body of the patient, and wherein the network interface is configured to forward ultrasound biosignals detected by the first signal detector.

5. The system of claim 1, wherein the first earbud is a wireless earbud, and wherein the network interface is a wireless network interface of the first earbud.

6. The system of claim 1, wherein the first earbud includes at least one motion sensor that facilitates positioning and orientation of the first signal detector relative to the body of the patient.

7. An auscultation system, the system comprising:

a first signal detector that is configured to detect biosignals including infrasonic and audible signals from a body of a patient, wherein the first signal detector includes:

a body; and a first earbud coupled to the body of the signal detector, wherein the first earbud includes an acoustic sensor that is configured to detect the biosignals from the body of the patient, via the body of the first signal detector;

a network interface configured to forward the biosignals from the first signal detector;

a remote device including an application programming interface (API) configured to receive the biosignals forwarded from the network interface; and a data analysis system configured to access the biosignals at the API;

wherein the body of the first signal detector includes a base that is configured to be positioned against the body of the patient near one or both lungs of the patient; and wherein the data analysis system is configured to classify pulmonary events based upon the biosignals in conjunction with lung sound models.

8. The system of claim 7, wherein the first earbud is a wireless earbud, and wherein the network interface is a wireless network interface of the first earbud.

9. An auscultation system, the system comprising:

a first signal detector that is configured to detect biosignals including infrasonic and audible signals from a body of a patient, wherein the first signal detector includes:

a body; and a first earbud coupled to the body of the signal detector, wherein the first earbud includes an acoustic sensor that is configured to detect the biosignals from the body of the patient, via the body of the first signal detector;

a network interface configured to forward the biosignals from the first signal detector;

a second earbud that is configured to detect biosignals including infrasonic and audible signals from the body of the patient, wherein the second earbud is configured to be placed at an ear canal of the patient and is configured to detect the biosignals from the ear canal, and wherein the network interface is configured to forward the biosignals from the second earbud;

a remote device including an application programming interface (API) configured to receive the biosignals forwarded from the network interface; and a data analysis system configured to access the biosignals at the API;

wherein the body of the first signal detector includes a base that is configured to be positioned against the body of the patient near an artery of the patient, and wherein the data analysis system is configured to determine a level of arterial and/or valvular stenosis of the artery based upon the biosignals.

10. The system of claim 9, further comprising a controller board that includes the network interface, wherein the network interface is a wireless interface, and wherein the first earbud and the second earbud are wireless earbuds.

11. The system of claim 9, wherein the first earbud and the second earbud each include at least one motion sensor that facilitates positioning and orientation of the first signal detector and the second signal detector relative to the body of the patient.

12. An auscultation system, the system comprising:

a first signal detector that is configured to detect biosignals including infrasonic and audible signals from a body of a patient, wherein the first signal detector includes:

a body; and a first earbud coupled to the body of the signal detector, wherein the first earbud includes an acoustic sensor that is configured to detect the biosignals from the body of the patient, via the body of the first signal detector;

a network interface configured to forward the biosignals from the first signal detector;

a second earbud that is configured to detect biosignals including infrasonic and audible signals from the body of the patient;

a second signal detector that includes a body and includes the second earbud. wherein the second earbud is coupled to the body of the second signal detector, and wherein the body of the second signal detector includes a base that is configured to be positioned against the body of the patient, and wherein the second signal detector is configured to send the biosignals to the network interface:

a remote device including an application programming interface (API) configured to receive the biosignals forwarded from the network interface; and a data analysis system configured to access the biosignals at the API;

wherein the first and the second signal detectors are configured to be positioned in a substantially collinear fashion at a distance apart from one another and their bases are configured to be positioned against the body of the patient near a same blood vessel; and wherein the data analysis system is configured to determine a pulse velocity of the patient based upon the biosignals.

13. The system of claim 12, further comprising a controller board that includes the network interface, wherein the network interface is a wireless interface, and wherein the first earbud and the second earbud are wireless earbuds.

14. The system of claim 12, wherein the first earbud and the second earbud each include at least one motion sensor that facilitates positioning and orientation of the first signal detector and the second signal detector relative to the body of the patient.

15. An auscultation system, the system comprising:

a first signal detector that is configured to detect biosignals including infrasonic and audible signals from a body of a patient, wherein the first signal detector includes:

a body; and a first earbud coupled to the body of the signal detector, wherein the first earbud includes an acoustic sensor that is configured to detect the biosignals from the body of the patient, via the body of the first signal detector;

a network interface configured to forward the biosignals from the first signal detector;

a second earbud that is configured to detect biosignals including infrasonic and audible signals from the body of the patient;

a second signal detector that includes a body and includes the second earbud, wherein the second earbud is coupled to the body of the second signal detector, and wherein the body of the second signal detector includes a base that is configured to be positioned against the body of the patient, and wherein the second signal detector is configured to send the biosignals to the network interface;

a remote device including an application programming interface (API) configured to receive the biosignals forwarded from the network interface; and a data analysis system configured to access the biosignals at the API;

wherein the base of the first signal detector is configured to be positioned against the body of a pregnant patient near a heart of the patient, and wherein the base of the second signal detector is configured to be positioned against the body of the patient near where a fetus of the patient resides; and wherein the data analysis system is configured to isolate a heartbeat of the patient and a heartbeat of the fetus based upon the biosignals.

16. The system of claim 15, further comprising a controller board that includes the network interface, wherein the network interface is a wireless interface, and wherein the first earbud and the second earbud are wireless earbuds.

17. The system of claim 15, wherein:

the body of the first signal detector includes a membrane that is configured to enable the coupling of the first earbud to the body of the first signal detector, to provide an acoustic seal between the first earbud and the body of the first signal detector, and to enable removeable attachment of the first earbud from the body of the first signal detector; and the body of the second signal detector includes a membrane that is configured to enable the coupling of the second earbud to the body of the second signal detector, to provide an acoustic seal between the second earbud and the body of the second signal detector, and to enable removeable attachment of the second earbud from the body of the second signal detector.

18. A method for acquiring biosignals, the method comprising:

providing a first signal detector that detects biosignals including infrasonic and audible signals from a body of a patient, the first signal detector including:

a body including a base; and a first earbud coupled to the body, the first earbud including an acoustic sensor detecting the biosignals from the body of the patient via the body of the first signal detector;

positioning the base against the body of a patient to receive biosignals;

forwarding the received biosignals toward a remote device across a network;

positioning the base of the first signal detector against the body of the patient near a heart of the patient;

accessing the biosignals at an application programming interface (API) presented by the remote device; and determining a heartbeat and heart sounds of the patient based upon the biosignals in conjunction with heart sound models.

19. A method for acquiring biosignals, the method comprising:

providing a first signal detector that detects biosignals including infrasonic and audible signals from a body of a patient, the first signal detector including:

a body including a base; and a first earbud coupled to the body, the first earbud including an acoustic sensor detecting the biosignals from the body of the patient via the body of the first signal detector;

positioning the base against the body of a patient to receive biosignals;

forwarding the received biosignals toward a remote device across a network;

positioning the base of the first signal detector against the body of the patient near one or more lungs of the patient;

accessing the biosignals at an application programming interface (API) presented by the remote device; and classifying pulmonary events based upon the biosignals in conjunction with lung sound models.

20. A method for acquiring biosignals, the method comprising:

providing a first signal detector that detects biosignals including infrasonic and audible signals from a body of a patient, the first signal detector including:

a body including a base; and a first earbud coupled to the body, the first earbud including an acoustic sensor detecting the biosignals from the body of the patient via the body of the first signal detector;

positioning the base against the body of a patient to receive biosignals;

forwarding the received biosignals toward a remote device across a network;

positioning a second earbud at an ear canal of the patient that detects the biosignals including infrasonic and audible signals from the body of the patient in the ear canal;

forwarding the biosignals detected by the second earbud toward the remote device across the network;

positioning the base of the first signal detector against the body of the patient near an artery of the patient;

accessing the biosignals from the first signal detector and the second earbud at an application programming interface (API) presented by the remote device; and determining a level of arterial and/or valvular stenosis of the artery based upon the biosignals.

21. A method for acquiring biosignals, the method comprising:

providing a first signal detector that detects biosignals including infrasonic and audible signals from a body of a patient, the first signal detector including:

a body including a base; and a first earbud coupled to the body, the first earbud including an acoustic sensor detecting the biosignals from the body of the patient via the body of the first signal detector;

positioning the base against the body of a patient to receive biosignals;

forwarding the received biosignals toward a remote device across a network;

positioning a second earbud at an ear canal of the patient that detects the biosignals including infrasonic and audible signals from the body of the patient in the ear canal;

forwarding the biosignals detected by the second earbud toward the remote device across the network;

positioning a base of a body of a second signal detector against the body of the patient to receive biosignals, the second earbud being coupled to the body of the second signal detector, the second earbud detecting biosignals including infrasonic and audible signals from the body of the patient;

forwarding the biosignals sent by the first and the second signal detectors toward the remote device across the network;

positioning the first and the second signal detectors in a substantially collinear fashion at a distance apart from one another, with their bases disposed against the body of the patient near a same blood vessel;

accessing the biosignals from the first and second signal detectors at an application programming interface (API) presented by the remote device; and determining a pulse velocity of the patient based upon the biosignals.

22. A method for acquiring biosignals, the method comprising:

providing a first signal detector that detects biosignals including infrasonic and audible signals from a body of a patient, the first signal detector including:

a body including a base; and a first earbud coupled to the body, the first earbud including an acoustic sensor detecting the biosignals from the body of the patient via the body of the first signal detector;

positioning the base against the body of a patient to receive biosignals;

forwarding the received biosignals toward a remote device across a network;

positioning a second earbud at an ear canal of the patient that detects the biosignals including infrasonic and audible signals from the body of the patient in the ear canal;

forwarding the biosignals detected by the second earbud toward the remote device across the network;

positioning a base of a body of a second signal detector against the body of the patient to receive biosignals, the second earbud being coupled to the body of the second signal detector, the second earbud detecting biosignals including infrasonic and audible signals from the body of the patient;

forwarding the biosignals sent by the first and the second signal detectors toward the remote device across the network;

positioning the base of the first signal detector against the body of a pregnant patient near a heart of the patient;

positioning the base of the second signal detector against the body of the patient near where a fetus of the patient resides;

accessing the biosignals from the first and second signal detectors at an application programming interface (API) presented by the remote device; and isolating a heartbeat of the patient and a heartbeat of the fetus based upon the biosignals.

* * * * *